(12) United States Patent
Aoki

(10) Patent No.: US 10,677,750 B2
(45) Date of Patent: *Jun. 9, 2020

(54) GAS DETECTION DEVICE

(71) Applicant: Toyota Jidosha Kabushiki Kaisha, Toyota-shi, Aichi-ken (JP)

(72) Inventor: Keiichiro Aoki, Shizuoka-ken (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 90 days.

This patent is subject to a terminal disclaimer.

(21) Appl. No.: 15/892,851

(22) Filed: Feb. 9, 2018

(65) Prior Publication Data

US 2018/0231493 A1 Aug. 16, 2018

(30) Foreign Application Priority Data

Feb. 13, 2017 (JP) .................................. 2017-023969

(51) Int. Cl.
| | |
|---|---|
| *G01N 27/406* | (2006.01) |
| *G01N 27/12* | (2006.01) |
| *G01N 27/407* | (2006.01) |
| *G01N 27/41* | (2006.01) |
| *G01M 15/10* | (2006.01) |
| *G01N 33/00* | (2006.01) |

(52) U.S. Cl.
CPC ....... *G01N 27/4067* (2013.01); *G01N 27/123* (2013.01); *G01N 27/4071* (2013.01); *G01N 27/4074* (2013.01); *G01N 27/41* (2013.01); *G01M 15/102* (2013.01); *G01N 33/0042* (2013.01); *Y02A 50/248* (2018.01)

(58) Field of Classification Search
CPC ...................... G01N 27/4074; F01N 2560/027
See application file for complete search history.

(56) References Cited

U.S. PATENT DOCUMENTS

| | | | |
|---|---|---|---|
| 8,393,316 B2* | 3/2013 | Kunihiro | ............... F01N 3/0842 123/697 |
| 2016/0146085 A1* | 5/2016 | Mizutani | ................. F01N 11/00 60/274 |
| 2018/0172624 A1* | 6/2018 | Aoki | .................. G01N 27/4074 |

FOREIGN PATENT DOCUMENTS

| | | | | |
|---|---|---|---|---|
| JP | 2015017931 | * | 1/2015 | ........... G01N 27/416 |
| JP | 2015017931 A | | 1/2015 | |

OTHER PUBLICATIONS

U.S. Appl. No. 15/796,219, filed Oct. 27, 2017; Inventors: Keiichiro Aoki et al.

(Continued)

*Primary Examiner* — Luan V Van
*Assistant Examiner* — Caitlyn Mingyun Sun
(74) *Attorney, Agent, or Firm* — Dinsmore & Shohl LLP

(57) ABSTRACT

A gas detection device includes a temperature control part configured to detect an element impedance by applying a high frequency voltage to an element part, and to control an electric power to be supplied to a heating part based on the detected element impedance. The temperature control part is configured, when the applied voltage control for SOx detection is being performed and at least a voltage decrease sweep is being performed, to perform a second element temperature control to stop detecting the element impedance to set the electric power to be supplied to the heating part to a predetermined electric power.

5 Claims, 15 Drawing Sheets

(56) References Cited

OTHER PUBLICATIONS

Non-Final Office Action dated Jul. 18, 2019 in U.S. Appl. No. 15/887,189, filed Feb. 2, 2018.
Final Office Action dated Dec. 13, 2019 in U.S. Appl. No. 15/887,189, filed Feb. 2, 2018.
Notice of Allowance dated Mar. 25, 2020 in U.S. Appl. No. 15/887,189.

* cited by examiner

US 10,677,750 B2

GAS DETECTION DEVICE

CROSS-REFERENCE TO RELATED APPLICATIONS

This application claims priority to Japanese Patent Application No. 2017-023969 filed on Feb. 13, 2017, the entire contents of which are incorporated herein by reference.

BACKGROUND

1. Field

The present disclosure relates to a gas detection device capable of determining whether or not sulfur oxide having a concentration equal to or higher than a predetermined concentration is contained in exhaust gas (gas to be detected) of an internal combustion engine, or capable of detecting a concentration of the sulfur oxide contained in the exhaust gas.

2. Description of the Related Art

Hitherto, there is widely used an air-fuel ratio sensor (also referred to as an "A/F sensor") configured to acquire an air-fuel ratio (A/F) of mixture in a combustion chamber based on a concentration of oxygen ($O_2$) contained in exhaust gas in order to control an internal combustion engine. As one type of the air-fuel ratio sensor, a limiting current type gas sensor is known.

Further, a sulfur oxide (hereinafter sometimes referred to as "SOx") concentration detection device (hereinafter referred to as a "related-art device") configured to detect a concentration of SOx in the exhaust gas through use of such a limiting current type gas sensor has been proposed (refer to, for example, Japanese Patent Application Laid-open Publication No. 2015-17931).

The related-art device includes a sensing cell (sometimes referred to as an "electrochemical cell" or an "element") using an oxygen pumping action of an oxygen ion conductive solid electrolyte. The related-art device is configured to apply a voltage between a pair of electrodes of the sensing cell to decompose gas components (for example, $O_2$, SOx, and $H_2O$, and hereinafter, also referred to as "oxygen-containing components") containing oxygen atom in the exhaust gas, to thereby generate oxide ions ($O^{2-}$). The related-art device is configured to detect a characteristic of a current flowing between the electrodes as a result of movement (oxygen pumping actin) of the oxide ions generated by the decomposition of the oxygen-containing components between the electrodes of the sensing cell.

More specifically, the related-art device is configured to perform an applied voltage sweep when it detects the SOx concentration.

Specifically, the related-art device is configured to perform the applied voltage sweep to increase/raise an applied voltage applied to the sensing cell from 0.4 V to 0.8 V and then decrease the applied voltage from 0.8 V to 0.4 V.

The related-art device is configured to use a difference between a reference current and a peak value so as to calculate the SOx concentration. The reference current is a "current (hereinafter, sometimes referred to as an "electrode current" or an "output current") flowing between the electrodes of the sensing cell" when the applied voltage reaches 0.8 V during the applied voltage sweep. The peak value is the minimum value of the output current in a period in which the applied voltage is being decreased from 0.8 V to 0.4 V during the applied voltage sweep.

However, the output current may also vary due to influence of the oxygen-containing components other than SOx contained in the exhaust gas. For example, a decomposition voltage of water ($H_2O$) is equal to or slightly higher than a decomposition voltage of sulfur oxide. Further, the concentration of the water in the exhaust gas varies in accordance with, for example, the air-fuel ratio A/F of the mixture. Therefore, it is difficult to eliminate the influence of the decomposition of the water on the output current from the output current to detect the output current which stems from (or corresponds to) the decomposition of the SOx component only.

Thus, there has been a demand for performing the applied voltage sweep, similarly to the related-art device, to acquire an "output current change which is not influenced by the oxygen-containing components other than SOx but is caused only by the SOx component", and for using the acquired output current change to accurately determine whether or not the sulfur oxide having a concentration equal to or higher than a predetermined concentration is contained (present) in the exhaust gas or to accurately detect/measure the concentration of the sulfur oxide in the exhaust gas (sometimes such a detection is referred to as a "SOx concentration detection").

Further, the output current change that the related-art device acquires varies depending on a temperature of the element. Therefore, it is preferable that the related-art device avoid a degradation in detection accuracy due to the temperature of the element. Therefore, the related-art device needs to maintain the element temperature at a predetermined temperature (predetermined temperature equal to or higher than a temperature at which the oxide ion conductivity of the solid electrolyte of the element appears).

In view of the above, by utilizing characteristic that the element impedance varies in accordance with the element temperature, the related-art device performs energization control of the heater through impedance feedback control using the element impedance, to thereby maintain the element temperature at the predetermined temperature. The element impedance is calculated based on the output current which is detected when a voltage having a predetermined high frequency is applied between the electrodes of the element.

However, when the related-art device performs the "SOx concentration detection", if the device acquires an "output current change, which is not influenced by the oxygen-containing components other than SOx, but is caused only by the SOx component" while performing the element temperature control, a problem described below may arise.

That is, when the related-art device applies a voltage having a predetermined high frequency between the electrodes of the element to detect the element impedance, a change/variation caused by the application of the high frequency voltage appears in the output current. For this reason, when the related-art device detects the element impedance, it is difficult for the elated-art device to acquire the accurate "output current change which is not influenced by the oxygen-containing components other than SOx but is caused only by the SOx component". As a result, there is a high possibility that the accuracy of the SOx concentration detection may be degraded.

SUMMARY

The present disclosure has been made in order to solve the above-mentioned problem, and therefore has an object to provide a gas detection device (hereinafter also referred to as a "present disclosure detection device) capable of accurately determining whether or not sulfur oxide having a concentration equal to or higher than a predetermined concentration is contained in exhaust gas or of accurately detecting the concentration of the sulfur oxide.

The present disclosure detection device comprises: an element part (40), provided in an exhaust gas passage (12) of an internal combustion engine, and having an electrochemical cell (41$c$) including a solid electrolyte body (41$s$) having oxide ion conductivity, a first electrode (41$a$), and a second electrode (41$b$) formed on respective surface of the solid electrolyte body, and a diffusion resistance body (61) made of a porous material through which exhaust gas flowing through the exhaust gas passage is allowed to pass, the element part being configured so that the exhaust gas flowing through the exhaust passage reaches the first electrode through the diffusion resistance body; a voltage application part (81) configured to apply a voltage between the first electrode and the second electrode; a current detection part (91) configured to detect an output current (Im) which is a current flowing between the first electrode and the second electrode; a measurement control part (20) configured to use the voltage application part to control an applied voltage which is the voltage applied between the first electrode and the second electrode, use the current detection part to acquire the output current, and perform, based on the acquired output current, a determination as to whether or not sulfur oxide having a concentration equal to or higher than a predetermined concentration is contained in the exhaust gas or a detection of a concentration of the sulfur oxide in the exhaust gas; an element impedance detection part (81, 89) configured to apply a high frequency voltage between the first electrode and the second electrode to thereby detect an impedance of the element part; a heating part (71) configured to generate heat having a heat amount corresponding to an electric power supplied thereto to thereby heat the element part; and a temperature control part (20) configured: to have the element impedance detection part perform or stop the detection of the element impedance by applying the high frequency voltage; and to control the electric power supplied to the heating part to thereby control a temperature of the element part. The measurement control part is configured: to use the voltage application part to perform applied voltage control for air-fuel ratio detection by setting the applied voltage to a voltage (Vaf) that brings the output current to a limiting current of oxygen, to thereby detect an air-fuel ratio (A/F) of mixture supplied to the internal combustion engine based on the output current acquired during a period in which the applied voltage control for the air-fuel ratio detection is being performed (Steps 1115 and 1130 shown in FIGS. 11 and 15); to use the voltage application part to perform applied voltage control for SOx detection (Step 1145 shown in FIGS. 11 and 15) which includes an applied voltage sweep at least for one cycle, the applied voltage sweep including a voltage increase sweep and a voltage decrease sweep, wherein the voltage increase sweep increases the applied voltage from a first voltage to a second voltage, the first voltage is within a first voltage range higher than a lower limit voltage in a region of the limiting current and lower than a decomposition start voltage of the sulfur oxide, and the second voltage is within a second voltage range higher than the decomposition start voltage of the sulfur oxide, and the voltage decrease sweep decreases the applied voltage from the second voltage to the first voltage, to acquire, based on the output current, a parameter (Id) correlating with a degree of a change in the output current caused by a current flowing between the first electrode and the second electrode owing to a phenomenon that sulfur adsorbed to the first electrode returns to sulfur oxide through a reoxidation reaction on the first electrode when the applied voltage becomes lower than the decomposition start voltage of the sulfur oxide while the voltage decrease sweep is being performed, the change in the output current being larger as the concentration of the sulfur oxide contained in the exhaust gas being larger (Step 1320 shown in FIGS. 12 and 13); and to perform, based on the acquired parameter, the determination (Step 1230 shown in FIG. 12) or the detection (Step 1310 shown in FIG. 13). The temperature control part is configured: to perform, while the applied voltage control for the air-fuel ratio detection is being performed, a first element temperature control to control the temperature of the element part by having the element impedance detection part detect the element impedance through applying the high frequency voltage and by controlling the electric power supplied to the heating part in such a manner that the detected impedance of the element part comes close to a target impedance (Step 1040 shown in FIG. 10; and Steps 1190 and 1192 shown in FIGS. 11, and 15); and to have the element impedance detection part stop applying the high frequency voltage to stop detecting the element impedance, and perform a second element temperature control to set the electric power supplied to the heating part to a predetermined electric power, while the applied voltage control for the SOx detection is being performed and at least the voltage decrease sweep is being performed (Step 1160 shown in FIG. 11 and Step 1560 shown in FIG. 15).

As a result of study of the inventor(s) of the present application, it has become clear that the "change in the output current" unlikely to be affected by the "oxide containing components other than the sulfur oxide" occurs owing to a phenomenon that the "sulfur adsorbed to the first electrode" returns to the sulfur oxide through the reoxidation reaction on the first electrode during the voltage decrease sweep. Further, it has become clear that a degree of the "change in the output current" significantly changes in accordance with a voltage decrease amount per a predetermined elapsed time period (namely, voltage decrease speed) during the voltage decrease sweep (see FIG. 5A and FIG. 5B). Mechanisms of the occurrences of those phenomena are inferred as follows.

The sulfur (decomposition product of the sulfur oxide) adsorbed to the first electrode as a result of the voltage increase sweep returns to the sulfur oxide through the reoxidation reaction on the first electrode during the voltage decrease sweep. When the voltage increase sweep is performed, the decomposition products (for example, hydrogen, which is a decomposition product of water) of the oxygen-containing components other than the sulfur oxide are not adsorbed to the first electrode. Therefore, such a phenomenon that the decomposition products of the oxygen-containing components other than the sulfur oxide return to the oxygen-containing components through the reoxidation on the first electrode does not substantially occur during the voltage decrease sweep.

Accordingly, the "change in the output current" generated by the phenomenon that the sulfur adsorbed to the first electrode returns to the sulfur oxide through the reoxidation reaction on the first electrode during the voltage decrease sweep is unlikely to be influenced by the oxygen-containing components other than the sulfur oxide. In other words, the "change in the output current" unlikely to be influenced by the oxygen-containing components other than the sulfur oxide occurs during the voltage decrease sweep.

However, when the voltage decrease speed (sweep speed) of the voltage decrease sweep is lower than a certain speed, the reoxidation reaction of the sulfur continuously and gradually progresses during the voltage decrease sweep, and the degree of the "change in the output current" hardly appears (is hardly observed) regardless of the concentration of the sulfur oxide.

In contrast, when the voltage decrease speed of the voltage decrease sweep is higher than the certain speed, the applied voltage decreases while the reoxidation reaction of sulfur has not progressed so much during the voltage decrease sweep. Thus, when the applied voltage reaches a voltage in a "certain voltage range in which the reoxidation reaction of the sulfur is significantly active (that is, predetermined voltage range lower than a decomposition start voltage of the sulfur oxide)", the reoxidation reaction of the sulfur quickly progresses (the speed of the reoxidation reaction of sulfur quickly increases, or an occurrence frequency of the reoxidation reaction of the sulfur quickly increases), and hence, the degree of the change in the output current is larger as the sulfur oxide concentration is higher. In other words, a significant current change for accurately detecting the sulfur oxide concentration appears (is observed).

In view of the above, the voltage decrease speed of the voltage decrease sweep is set to a "speed which allows the speed of the reoxidation reaction to quickly increase when and after the applied voltage reaches the voltage which is within the first voltage range and is higher than the first voltage". As a result, the change in the output current that is not influenced by the oxygen-containing components other than the sulfur oxide appears more significantly (greatly) as the sulfur oxide concentration is higher.

The present disclosure detection device is configured to, based on the output current, acquire a parameter correlating with a "degree of the change in the output current" caused by such a reoxidation reaction of the sulfur. Thus, this parameter is a parameter which varies in accordance with (depending on) the concentration of sulfur oxide contained in the exhaust gas.

Further, the present disclosure detection device is configured to determine whether or not the sulfur oxide having a concentration equal to or higher than a predetermined concentration is contained in the exhaust gas based on the acquired parameter, or to detect the concentration of the sulfur oxide in the exhaust gas based on the acquired parameter. Thus, the present disclosure detection device can accurately determine the absence/presence of the "sulfur oxide having a concentration equal to or higher than the predetermined concentration" contained in the exhaust gas, or accurately detect the concentration of the sulfur oxide contained in the exhaust gas.

Meanwhile, the parameter may be fluctuated/affected by the temperature of the element part. Therefore, it is preferable that the present disclosure detection device acquire the parameter while avoiding the "variation in the output current" caused by the temperature of the element part, in order to avoid degradation in the detection accuracy. Therefore, the present disclosure detection device needs to maintain the temperature of the element part at a predetermined temperature (which is equal to or higher than the temperature at which the oxide ion conductivity of the solid electrolyte body of the element part appears).

In view of the above, the present disclosure detection device utilizes a characteristic that an impedance of the element part varies in accordance with the temperature of the element part. The present disclosure detection device is configured to perform energization control of the heater through the feedback control using the element impedance, to thereby maintain the temperature of the element part at the predetermined temperature.

However, when the present disclosure detection device acquires the above parameter based on the output current for the SOx concentration detection while performing the element temperature control, a problem described below may arise.

That is, since the present disclosure detection device applies the high frequency voltage between the electrodes of the element to detect the impedance of the element part, the output current varies due to the applied high frequency voltage. Thus, when the present disclosure detection device detects the impedance of the element part, it is difficult for the present disclosure detection device to acquire the parameter which accurately varies in accordance with the sulfur oxide concentration in the exhaust gas. For this reason, the accuracy of the SOx concentration detection is likely to be degraded, leading to the undesired result.

In view of the above, the temperature control part of the present disclosure detection device is configured to have the element impedance detection part stop applying the high frequency voltage to stop detecting the element impedance, and perform a second element temperature control to set the electric power supplied to the heating part to a predetermined electric power, while the applied voltage control for the SOx detection is being performed and at least the voltage decrease sweep is being performed.

Therefore, it is possible to reduce the possibility that it becomes difficult to acquire the parameter that accurately changes in accordance with the sulfur oxide concentration of the exhaust gas. As a result, the determination as to whether or not the concentration of the sulfur oxide in the exhaust gas has a value equal to or higher than the predetermined value or the detection of the concentration of the sulfur oxide in the exhaust gas can be performed with high accuracy.

In one of aspects of the present disclosure detection device, the temperature control part is configured to perform the first element temperature control (Step 1190 shown in FIG. 11) when the voltage increase sweep is being performed (refer to a "No" determination at step 1155 shown in FIG. 11) while the applied voltage control for SOx detection is being performed.

According to the above-mentioned one aspect, the first temperature control is not performed while the voltage decrease sweep is performed. Therefore, it is possible to reduce the possibility that it becomes difficult to acquire the parameter that accurately changes in accordance with the sulfur oxide concentration of the exhaust gas. As a result, the determination as to whether or not the concentration of the sulfur oxide in the exhaust gas has a value equal to or higher than the predetermined value or the detection of the concentration of the sulfur oxide in the exhaust gas can be performed with high accuracy.

In one of the aspects of the present disclosure detection device: the temperature control part is configured: to change an energization control amount to thereby control the electric power supplied to the heating part; and to perform the second element temperature control (Step 1160 shown in FIG. 11 or Step 1560 shown in FIG. 15): by keeping the energization control amount at an amount at a time point a predetermined time before the first element temperature control is stopped; or by keeping the energization control amount at a preset constant amount.

According to the above-mentioned aspect, while the second element temperature control is being performed, the temperature of the element part is maintained at a temperature suitable for detecting the SOx concentration. As a result, the determination as to whether or not the concentration of the sulfur oxide in the exhaust gas has a value equal to or higher than the predetermined value or the detection of the concentration of the sulfur oxide in the exhaust gas can be performed with high accuracy.

In one of the aspects of the present disclosure detection device: the temperature control part is configured to perform the second element temperature control so as to supply electric power having an amount which is set in advance to the heating part in a period when the element impedance detection is stopped.

According to the above-mentioned aspect, while the second element temperature control is being performed, the temperature of the element part is maintained at a temperature suitable for detecting the SOx concentration. As a result, the determination as to whether or not the concentration of the sulfur oxide in the exhaust gas has a value equal to or higher than the predetermined value or the detection of the concentration of the sulfur oxide in the exhaust gas can be performed with high accuracy.

In one of the aspects of the present disclosure detection device: a voltage decrease speed of the voltage decrease sweep is set at a speed which has a rate of the reoxidation reaction quickly increase when and immediately after the applied voltage becomes a voltage in the first voltage range and higher than the first voltage.

According to the above-mentioned aspect, the "change in the output current" that is not influenced by the oxygen-containing components other than the sulfur oxide more significantly appears as the sulfur oxide concentration is higher. Therefore, based on the parameter correlating with the degree of the change in the output current, the determination as to whether or not the concentration of the sulfur oxide in the exhaust gas has a value equal to or higher than the predetermined value or the detection of the concentration of the sulfur oxide in the exhaust gas can be performed with high accuracy.

In the above description, for easier understanding of the present disclosure, the terms and/or reference symbols used in embodiments of the present disclosure described later are enclosed in parentheses and assigned to the components of the present disclosure corresponding to the embodiments. However, the constituent elements of the present disclosure are not limited to the embodiments defined by the terms and/or reference symbols. Other objects, other features, and accompanying advantages of the present disclosure are easily understandable from the description of the embodiments of the present disclosure to be given with reference to the following drawings.

DETAILED DESCRIPTION

Now, with reference to the accompanying drawings, a gas detection device according to each embodiment of the present disclosure is described. In all figures of the embodiments, the same or corresponding parts are denoted by the same reference symbols.

First Embodiment

Figure 1:
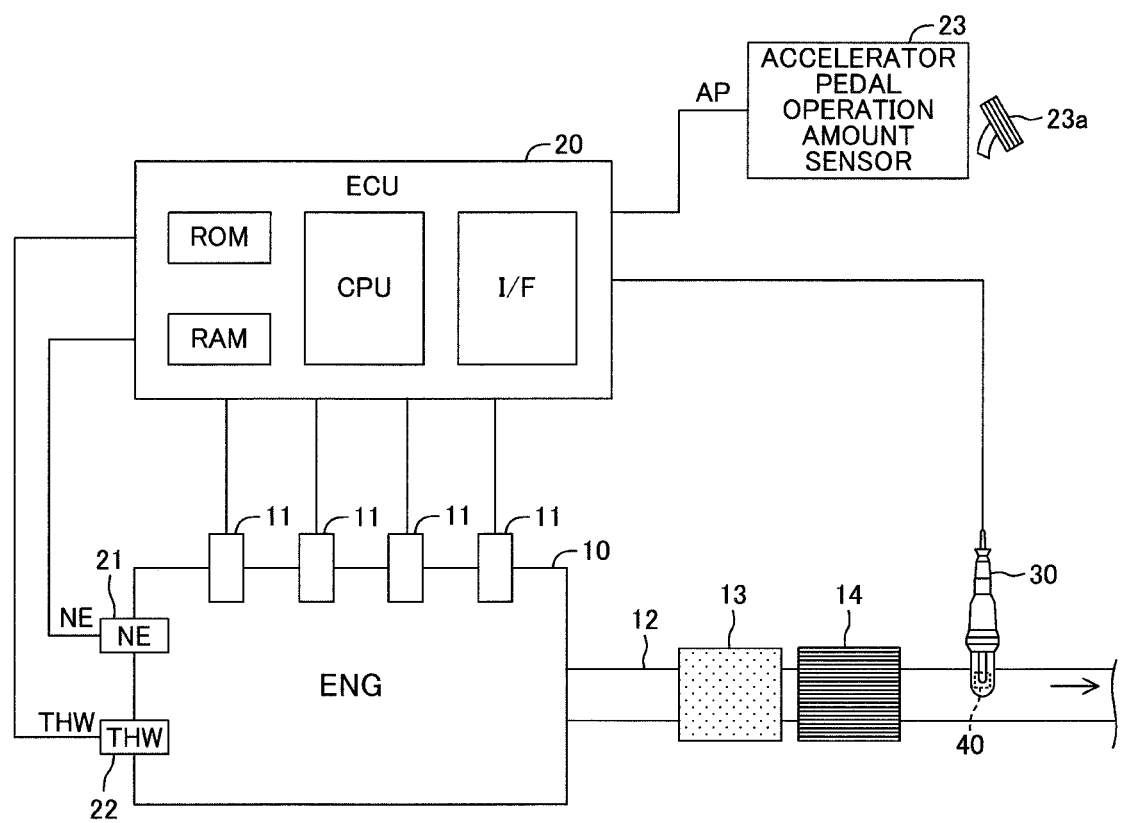
FIG. 1 is a schematic configuration diagram for illustrating a gas detection device according to a first embodiment of the present disclosure, and an internal combustion engine to which the gas detection device is applied.

A description is now given of a gas detection device (hereinafter sometimes referred to as a "first detection device") according to a first embodiment of the present disclosure. The first detection device is applied to an "internal combustion engine 10 illustrated in FIG. 1" installed on a vehicle (not shown).

The internal combustion engine 10 is a well-known diesel engine. The internal combustion engine 10 includes combustion chambers (not shown) and fuel injection valves (injector) 11. The fuel injection valves 11 are arranged on a cylinder head part so as to inject fuel into the combustion chambers. The fuel injection valve 11 is configured to directly inject fuel into the combustion chamber in accordance with an instruction of the ECU 20 described later. An exhaust pipe 12 is connected to an end of an exhaust manifold (not shown) which is connected to exhaust ports communicating to the combustion chambers (not shown). The exhaust ports, the exhaust manifold, and the exhaust pipe 12 form an exhaust gas passage through which the exhaust gas exhausted from the combustion chambers flows. A diesel oxidation catalyst (DOC) 13 and a diesel particulate filter (DPF) 14 are disposed/arranged in the exhaust pipe 12.

The DOC 13 is an exhaust gas purification catalyst. Specifically, the DOC 13 uses precious metal, for example, platinum or palladium, as a catalyst to oxide unburnt components (HC and CO) in the exhaust gas, thereby purifying the exhaust gas. In other words, HC is oxidized to be water and $CO_2$ by the DOC 13, and CO is oxidized to be $CO_2$ by the DOC 13.

The DPF 14 is arranged/disposed at a position downstream of the DOC 13. The DPF 14 is a filter for trapping particulates in the exhaust gas. Specifically, the DPF 14 includes a plurality of passages formed by a porous material (e.g., partitions formed by cordierite, which is a type of ceramic). The DPF 14 is configured to collect the particulates contained in the exhaust gas passing through the partitions, on porous surfaces of the partitions.

The first detection device includes the ECU 20. The ECU 20 is an electronic control circuit including, as a main component, a microcomputer including a CPU, a ROM, a RAM, a backup RAM, and an interface (I/F). The CPU is configured to execute instructions (routines) stored in a memory (ROM) to implement predetermined functions.

The ECU 20 is connected to various actuators (fuel injection valves 11 and the like) of the internal combustion engine 10. The ECU 20 is configured to transmit drive (instruction) signals to those actuators, to thereby control the internal combustion engine 10. Further, the ECU 20 is connected to various sensors described below to receive signals from those sensors.

Engine rotation speed sensor 21: an engine rotation speed sensor (hereinafter referred to as an "NE sensor") 21 is configured to measure a rotation speed (engine rotational speed) NE of the internal combustion engine 10 so as to generate/output a signal representing the engine rotation speed NE.

Water temperature sensor 22: a water temperature sensor 22 is arranged in a cylinder block part. The water temperature sensor 22 is configured to measure a temperature (coolant temperature THW) of coolant for cooling the internal combustion engine 10 to generate/output a signal representing the coolant temperature THW.

Accelerator pedal operation amount sensor 23: an accelerator pedal operation amount sensor 23 is configured to detect an operation amount (accelerator opening degree) AP of an accelerator pedal 23a of the vehicle to generate/output a signal representing the accelerator pedal operation amount AP.

Gas sensor 30: a gas sensor 30 is a limiting current type gas sensor of one cell type, and is arranged/disposed in the exhaust pipe 12 constructing an exhaust passage of the engine 10. The gas sensor 30 is arranged/disposed at a position downstream of the DOC 13 and the DPF 14, both interposed in the exhaust pipe 12.

(Construction of Gas Sensor)

Figure 2:
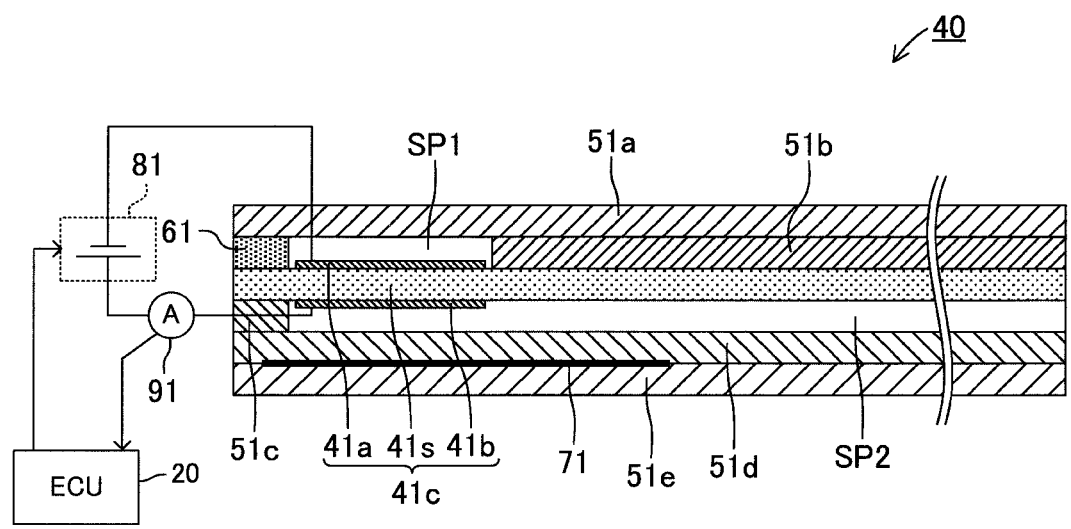
FIG. 2 is a schematic sectional view for illustrating an example of a configuration of an element part of a gas sensor illustrated in FIG. 1.

With reference to FIG. 2, a description is now given of a construction of the gas sensor 30. An element part 40 which the gas sensor 30 comprises includes a solid electrolyte body 41s, a first alumina layer 51a, a second alumina layer 51b, a third alumina layer 51c, a fourth alumina layer 51d, a fifth alumina layer 51e, a diffusion resistance part (diffusion speed regulation layer) 61, and a heater 71.

The solid electrolyte body 41s contains zirconia and the like, and is a thin plate body having the oxide ion conductivity. The zirconia forming the solid electrolyte body 41s may contain elements such as scandium (Sc) and yttrium (Y).

The first to fifth alumina layers 51a to 51e are dense (gas impermeable) layers (dense thin plate bodies) containing alumina.

The diffusion resistance part 61 is a porous diffusion speed regulation layer, and is a gas permeable layer (thin plate body). The heater 71 is a thin plate body made of cermet containing platinum (Pt) and ceramic (e.g., alumina), and is a heat generation body for generating heat through energization (current supply). The heater 71 is connected to a power supply (not shown) installed on the vehicle through lead wires (not shown). The energization of the heater 71 is controlled by the ECU 20 so that an "amount of an electric power supplied to the heater 71 from the power supply" is controlled. Thereby, the heater 71 is configured to change a heat generation amount through the control of the amount of the electric energy.

The layers of the element part 40 are layered from the bottom in a sequence of the fifth alumina layer 51e, the fourth alumina layer 51d, the third alumina layer 51c, the solid electrolyte body 41s, the diffusion resistance part 61 and the second alumina layer 51b, and the first alumina layer 51a.

An internal space SP1 is a space, which is formed by the first alumina layer 51a, the solid electrolyte body 41s, the diffusion resistance part 61, and the second alumina layer 51b, and into which the exhaust gas of the internal combustion engine 10 is introduced as the gas to be detected via the diffusion resistance part 61. In other words, the internal space SP1 communicates to an inside of the exhaust pipe 12 of the internal combustion engine 10 via the diffusion resistance part 61. Thus, the exhaust gas in the exhaust pipe 12 is introduced into the internal space SP1 as the gas to be detected.

A first atmosphere introduction passage SP2 is formed by the solid electrolyte body 41s, the third alumina layer 51c, and the fourth alumina layer 51d, and is opened to the atmosphere outside the exhaust pipe 12.

The first electrode 41a is fixed onto a surface (specifically, surface of the solid electrolyte body 41s defining the internal space SP1) on one side of the solid electrolyte body 41s. The first electrode 41a is a negative electrode. The first electrode 41a is a porous cermet electrode containing platinum (Pt) as a main component.

The second electrode 41b is fixed onto a surface (specifically, surface of the solid electrolyte body 41s defining the first atmosphere introduction passage SP2) on the other side of the solid electrolyte body 41s. The second electrode 41b is a positive electrode. The second electrode 41b is a porous cermet electrode containing platinum (Pt) as a main component.

The first electrode 41a and the second electrode 41b are arranged so as to face each other through the solid electrolyte body 41s. In other words, the first electrode 41a, the second electrode 41b, and the solid electrolyte body 41s construct an electrochemical cell 41c having an oxygen discharging capability through an oxygen pumping action. The electrochemical cell 41c is heated to an activation temperature by the heater 71.

Each of the solid electrolyte body 41s and the respective layers of the first to fifth alumina layers 51a to 51e is formed into a sheet form through, for example, the doctor blade method, the extrusion, or the like. The first electrode 41a, the second electrode 41b, wires for the energization to those electrodes, and the like are formed by, for example, the screen print method. The element part 40 having the above-mentioned structure is integrally manufactured by layering those sheets as described above, and firing them.

The materials forming the first electrode 41a are not limited to the above-mentioned materials, and may be selected from materials containing an element from the platinum group, for example, platinum (Pt), rhodium (Rh), palladium (Pd), alloy thereof, or the like as main components. The material forming the first electrode 41a is not particularly limited as long as the material can reductively decompose SOx contained in the exhaust gas introduced into the internal space SP1 via the diffusion resistance part 61 when a voltage (specifically, voltage equal to or higher than approximately 0.6 V) equal to or higher than a SOx decomposition start voltage is applied between the first electrode 41a and the second electrode 41b.

The gas sensor 30 further includes a power supply circuit 81 and an ammeter 91. The power supply circuit 81 and the ammeter 91 are connected to the above-mentioned ECU 20.

The power supply circuit 81 is configured to apply a predetermined voltage (hereinafter also referred to as "applied voltage Vm") between the first electrode 41a and the second electrode 41b so that an electric potential of the second electrode 41b is higher than an electric potential of the first electrode 41a. The power supply circuit 81 is configured to be controlled by the ECU 20 so as to change the applied voltage Vm.

The ammeter 91 is configured to measure an output current (electrode current) Im, which is a current flowing between the first electrode 41a and the second electrode 41b (that is, current flowing through the solid electrolyte body 41s), and output a measured value to the ECU 20.

The ECU 20 is configured to calculate an impedance (hereinafter, also referred to as an "element impedance") of the element part 40 based on an electrode current Im detected when a predetermined high frequency voltage is applied between the first electrode 41a and the second electrode 41b.

The ECU 20 can adjust electric power supplied to the heater 71 by controlling the energization to the heater 71. Specifically, the ECU 20 can adjust the electric power to be supplied to the heater 71 by duty control. As a result, the ECU 20 can control the temperature of the element part 40. In other words, the ECU 20 constitutes a temperature control part.

<Outline of Operation>

An outline of an operation performed by the first detection device will next be described. The first detection device is configured to detect an oxygen concentration of the exhaust gas (gas to be detected) discharged from the internal combustion engine 10. The first detection device is configured to detect an air-fuel ratio (A/F) of mixture in the combustion chamber of the internal combustion engine 10 based on the oxygen concentration in the exhaust gas. Hereinafter, the air-fuel ratio of the mixture in the combustion chamber of the internal combustion engine 10 is referred to as an "air-fuel ratio A/F of the engine", or simply as an "air-fuel ratio A/F". Further, the first detection device is configured to determine absence/presence of "SOx having a concentration equal to or higher than a predetermined concentration" which is contained in the exhaust gas. The first detection device needs to take some seconds from a detection start to a detection end of the absence/presence of SOx having the concentration equal to or higher than the predetermined concentration, and thus is configured to determine the absence/presence of SOx having the concentration equal to or higher than the predetermined concentration under a state in which the air-fuel ratio A/F of the engine is stable. As the predetermined concentration, an arbitrary concentration higher than 0% and corresponding to a desired detection level is selected.

Figure 3A:
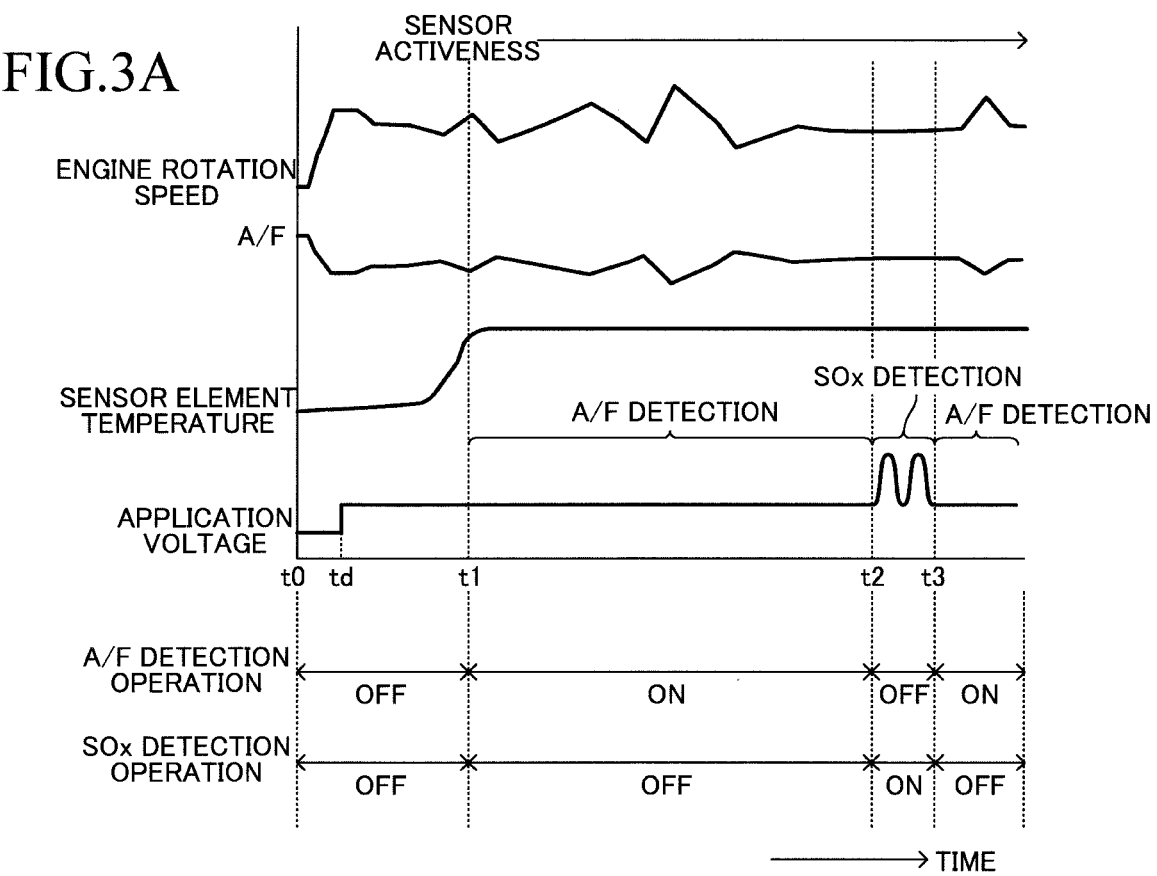
FIG. 3A is a time chart for illustrating an overview of an operation of the gas detection device according to the first embodiment of the present disclosure.

Specifically, as illustrated in FIG. 3A, at a time point t0 at which the internal combustion engine 10 is started, the first detection device starts the control for the heater 71 so that the solid electrolyte body 41s is heated by the heater 71. As a result, the solid electrolyte body 41s is heated so that the temperature of the electrolyte body 41s is raised to a predetermined temperature equal to or higher than a temperature (hereinafter sometimes referred to as an "activation temperature") at which oxide ion conductivity appears.

At a time point t1 at which the temperature (sensor element temperature) of the solid electrolyte body 41s becomes equal to or higher than the activation temperature, in other words, when the gas sensor 30 enters an active state, the first detection device starts processing for detecting the oxygen concentration of the exhaust gas to acquire/detect the air-fuel ratio A/F of the engine based on the detected oxygen concentration. At a time point td between the time point t0 and the time point t1, the first detection device starts applying a voltage (specifically, 0.3 V) for the oxygen concentration (A/F) detection which is suitable for detecting the oxygen concentration between the first electrode 41a and the second electrode 41b. This application of the voltage for detecting the oxygen concentration is sometimes referred to as "applied voltage control for the A/F detection". In other words, the first detection device sets the applied voltage Vm to a voltage for the oxygen concentration detection. When the temperature of the solid electrolyte body 41s is equal to or higher than the activation temperature, and the applied voltage Vm is set to the voltage for the oxygen concentration detection, the oxygen molecules are decomposed, and the oxygen pumping action thus appears. However, gasses of the oxygen-containing components (including SOx) other than the oxygen are not decomposed at this point in time.

The first detection device continuously detects the oxygen concentration from the time point t11 so as to thereby monitor the air-fuel ratio A/F of the engine. Thereafter, when a SOx detection start condition is satisfied (that is, when the air-fuel ratio A/F of the engine enters/becomes a stable state, and other conditions described later are simultaneously satisfied) at a time point t2, the first detection device starts processing for detecting the SOx concentration in the exhaust gas. It should be noted that the "SOx concentration detection" in the present specification means not only a detection (measurement) of the concentration of SOx contained in the exhaust gas but also an acquisition of a parameter representing the concentration of SOx contained in the exhaust gas (a parameter indicative of SOx concentration of the exhaust gas). As described later, the first detection device is configured to acquire the parameter representing the SOx concentration in the exhaust gas (i.e., the parameter varying in accordance with the SOx concentration), and use the parameter to determine whether or not the SOx having the concentration equal to or higher than the predetermined concentration is contained in the exhaust gas.

As described, in the period from the time point t1 to a time point immediately before the time point t2, the first detection device detects the air-fuel ratio A/F of the engine. The first detection device stops detecting the air-fuel ratio A/F of the engine at the time point t2, at which the device starts the SOx concentration detection.

In a period from the time point t2 to a time point immediately before a time point t3, the first detection device performs applied voltage control for the SOx concentration detection. Specifically, the first detection device performs an applied voltage sweep in a predetermined sweep voltage range. In other words, the first detection device performs a "voltage increase sweep to gradually increase the applied voltage Vm from a first voltage V1 to a second voltage V2", and then performs a "voltage decrease sweep to gradually decrease the applied voltage Vm from the second voltage V2 to the first voltage V1". The first detection device is configured to perform the applied voltage sweep for a plurality of cycles (e.g., two cycles), the one cycle of the applied voltage sweep including a single operation of the voltage increase sweep and a single operation of the voltage decrease sweep. It should be noted that the first detection device may perform only one cycle of the applied voltage sweep for the SOx concentration detection.

Figure 3B:
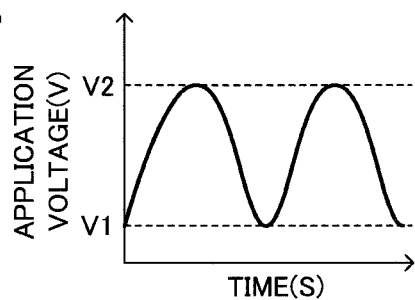
FIG. 3B is a graph for showing a waveform of an applied voltage exhibited when SOx detection is performed.

More specifically, as shown in FIG. 3B, the first detection device is configured to apply a voltage having a waveform of a sinusoidal wave between the first electrode 41a and the second electrode 41b, to thereby perform the applied voltage sweep. The voltage waveform is not limited to the sinusoidal wave shown in FIG. 3B, and various waveforms may be employed. For example, the voltage waveform may be a non-sinusoidal wave (waveform similar to a voltage waveform observed when a capacitor is charged and discharged) shown in the graph of FIG. 3C.

When the SOx concentration detection is finished at the time point t3, the first detection device resumes the processing for detecting the air-fuel ratio A/F of the engine. In other words, the first detection device sets the applied voltage Vm to the voltage (0.3 V) for the oxygen concentration detection at the time point t3.

(A/F Detection)

An operation of the first detection device when detecting the air-fuel ratio A/F of the engine will next be described. The first detection device is configured to set the applied voltage Vm to the voltage (e.g., 0.3 V) for the oxygen concentration detection so that the first electrode 41a is at a low electric potential and the second electrode 41b is at a high electric potential in order to acquire the air-fuel ratio A/F of the engine when the gas sensor 30 enters the state in which the sensor is active. In other words, the first electrode 41a functions as a negative electrode, and the second electrode 41b functions as a positive electrode. The voltage for the oxygen concentration detection is set to a voltage, that is equal to or higher than a voltage (decomposition start voltage) at which the decomposition of the oxygen ($O_2$) starts on the first electrode 41a, and at which a limiting current of the oxygen described later is observed, and that is lower than decomposition start voltages of the oxygen-containing components other than the oxygen. As a result, the oxygen contained in the exhaust gas is reductively decomposed into oxide ions ($O^{2-}$) on the first electrode 41a.

The oxide ions are conducted to the second electrode 41b via the solid electrolyte body 41s so as to become oxygen ($O_2$), and are then exhausted/discharged into the atmosphere via the first atmosphere introduction passage SP2. As described above, the movement of the oxygen through the conduction of the oxide ion from the negative electrode (first electrode 41a) to the positive electrode (second electrode 41b) via the solid electrolyte body 41s is referred to as the "oxygen pumping action".

As a result of the conduction of the oxygen ion caused by this oxygen pumping action, a current flows between the electrode 41a and the electrode 41b. The current flowing between the electrode 41a and the electrode 41b is referred to as an "output current Im (or an electrode current Im)". Generally, the output current Im has a tendency that the current Im increases as the applied voltage Vm increases. However, since the flow amount of the exhaust gas that reaches the first electrode 41a is restricted by the diffusion resistance part 61, a consumption speed of the oxygen caused by the oxygen pumping action eventually becomes higher than a supplying speed of the oxygen to the first electrode 41a. In other words, the reductive decomposition action of the oxygen on the first electrode 41a (negative electrode) enters/becomes a diffusion speed regulated state.

When the reductive decomposition reaction of the oxygen on the first electrode 41a enters/becomes the diffusion speed regulated state, the output current Im does not increase and becomes substantially constant even if the applied voltage Vm is increased. This property is referred to as a "limiting current characteristic". A range of the applied voltage when the limiting current characteristic appears (is observed) is referred to as a "limiting current range". Further, the output current Im in the limiting current range is referred to as a "limiting current". A magnitude (limiting current value) of the limiting current with respect to the oxygen corresponds to the supplying speed of the oxygen to the first electrode 41a (negative electrode). As described above, the flow rate of the exhaust gas that reaches the first electrode 41a is maintained to be constant by the diffusion resistance part 61, and hence the supplying speed of the oxygen to the first electrode 41a corresponds to the concentration of the oxygen contained in the exhaust gas.

Thus, in the gas sensor 30, the output current (limiting current) Im corresponds to the concentration of the oxygen contained in the exhaust gas when the applied voltage Vm is set to the "predetermined voltage (specifically, 0.3 V) in the limiting current range of the oxygen". In this manner, the first detection device is configured to use the limiting current characteristic of the oxygen to detect the concentration of the oxygen contained in the exhaust gas serving as the gas to be detected. Meanwhile, the air-fuel ratio A/F of the engine and the concentration of the oxygen in the exhaust gas have a one-to-one relationship. Thus, the first detection device is configured to store this relationship in the ROM in advance, and acquire the air-fuel ratio A/F of the engine based on the relationship and the detected oxygen concentration. It should be noted that the first detection device may be configured to store a relationship between the limiting current of the oxygen and the air-fuel ratio A/F of the engine in the ROM in advance, and to acquire the air-fuel ratio A/F of the engine based on the relationship and the detected limiting current of the oxygen.

(SOx Concentration Detection)

[Detection Principle]

A method for detecting the SOx concentration in the exhaust gas (gas to be detected) will next be described. The above-mentioned oxygen pumping action also occurs for the oxygen-containing components (compounds), for example, "SOx (sulfur oxide), $H_2O$ (water), and the like" that contain oxygen atoms in molecules. In other words, when a voltage equal to or higher than a decomposition start voltage of each of those compounds Is applied between the first electrode 41a and the second electrode 41b, each of the compounds is reductively decomposed, resulting in generation of oxide ions. The oxide ion is conducted from the first electrode 41a to the second electrode 41b through the "oxygen pumping action". As a result, the output current Im flows between the first electrode 41a and the second electrode 41b.

However, the concentration of SOx contained in the exhaust gas is extremely low, and thus, the current caused by the decomposition of SOx contained in the exhaust gas is also very small. Further, a current due to the decomposition of the oxygen-containing components (e.g., water, carbon dioxide) other than SOx also flows between the first electrode 41a and the second electrode 41b. Therefore, it is difficult to accurately/precisely detect the output current due only to SOx contained in the exhaust gas.

In view of the above, the inventor(s) of the present application has/have obtained through extensive study such knowledge that the SOx concentration can accurately/precisely be detected by performing the applied voltage sweep, the one cycle of applied voltage sweep including the voltage increase sweep and the "voltage decrease sweep at a predetermined sweep speed".

The voltage increase sweep is a process for gradually increasing the applied voltage Vm from the first voltage V1 to the second voltage V2. The voltage decrease sweep is a process for gradually decreasing the applied voltage Vm from the second voltage V2 to the first voltage V1. Each of the first voltage V1 and the second voltage V2 is an electric potential of the second electrode 41b with respect to the electric potential of the first electrode 41a as a reference, and is a positive voltage value.

The first voltage V1 is set to a voltage in a voltage range (hereinafter also referred to as a "first voltage range") lower than the decomposition start voltage (approximately 0.6 V) of SOx and higher than a minimum value of the applied voltage in the limiting current range of oxygen. The minimum value of the applied voltage in the limiting current range of oxygen varies depending on the air-fuel ratio A/F of the engine, and therefore, a lower limit value of the first voltage range may be changed in accordance with the air-fuel ratio A/F of the engine. Specifically, the lower limit value of the first voltage range is a voltage in a range, for example, from 0.2 V to 0.45 V, and the upper limit voltage of the first voltage range is 0.6 V. In other words, the first voltage is a voltage selected from a range from a voltage which is equal to or higher than 0.2 V to a voltage lower than 0.6 V.

The second voltage V2 is set to a voltage in a voltage range (hereinafter also referred to as a "second voltage range") higher than the decomposition start voltage (approximately 0.6 V) of SOx, and lower than an upper limit voltage (2.0 V) within a range in which the solid electrolyte body 41s is not destructed. In other words, the second voltage V2 is a voltage selected from the range from a voltage higher than 0.6 V to a voltage equal to or lower than 2.0 V.

Figure 4A:
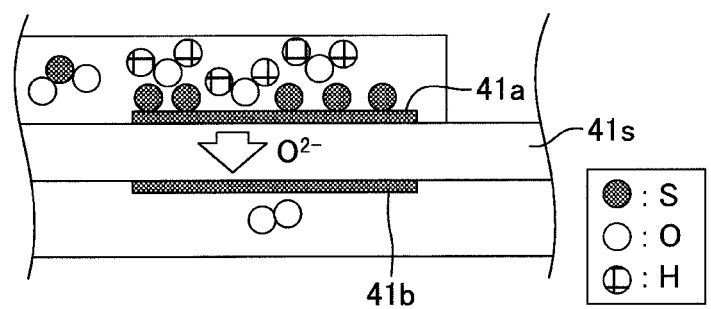
FIG. 4A is a schematic diagram for Illustrating decomposition reaction of SOx generated in the element part.

As illustrated in FIG. 4A, SOx contained in the exhaust gas is reductively decomposed into S and $O^{2-}$ on the first electrode 41a (negative electrode) when the applied voltage Vm applied between the first electrode 41a and the second electrode 41b becomes equal to or higher than the decomposition start voltage of SOx while the voltage increase sweep is being performed. As a result, a reductive decomposition product (S (sulfur)) of SOx is adsorbed to the first electrode 41a (negative electrode).

Figure 4B:
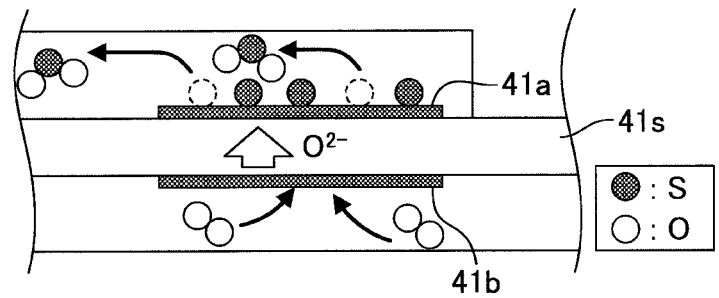
FIG. 4B is a schematic diagram for illustrating a reoxidation reaction of sulfur generated in the element part.

As illustrated in FIG. 4B, a reaction (hereinafter sometimes referred to as a "reoxidation reaction of S (sulfur)") occurs where S adsorbed to the first electrode 41a (negative electrode) and $O^{2-}$ react with each other to generate SOx, when the applied voltage Vm becomes lower than the decomposition start voltage of SOx while the voltage decrease sweep is being performed. The "reoxidation reaction of S" makes the output current Im vary as described later. This change/variation in the output current Im owing to the "reoxidation reaction of S" is referred to as a "reoxidation current change".

Figure 5A:
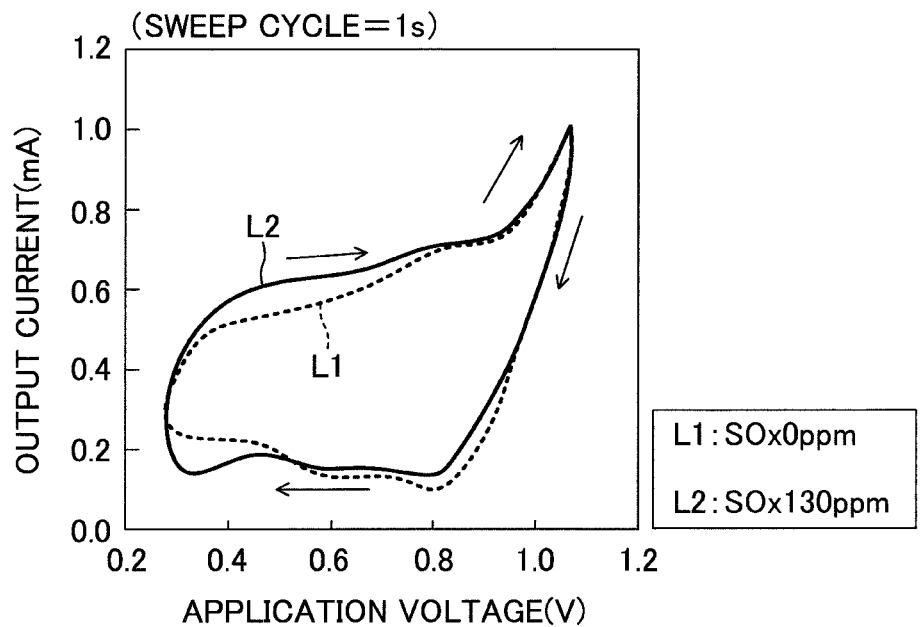
FIG. 5A is a graph for showing a relationship between an applied voltage and an output current.
Figure 5B:
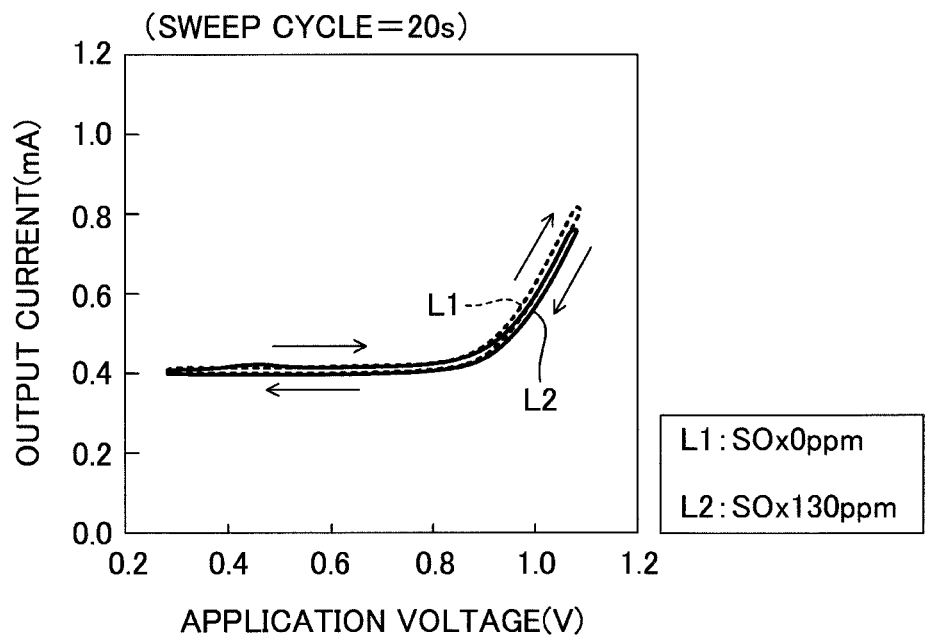
FIG. 5B is a graph for showing a relationship between the applied voltage and the output current.

Through a study of the inventor(s) of the present application, it has become clear that there are cases where a significant reoxidation current change does not appear in the SOx concentration detection depending on the sweep speed (voltage decrease amount per a predetermined elapsed time) of the voltage decrease sweep. With reference to FIG. 5A and FIG. 5B, a description is now given of this point.

FIG. 5A is a schematic graph for showing a relationship between the applied voltage Vm and the output current Im when the applied voltage sweep is performed while a sweep cycle (which is a sum of a time period required for the voltage increase sweep and a time period required for the voltage decrease sweep, namely, a cycle of the applied voltage sweep) is set to one second. FIG. 5B is a schematic graph for showing the relationship between the applied voltage Vm and the output current Im when the applied voltage sweep is performed at a sweep speed (sweep cycle: 20 seconds) lower than that in the example shown in FIG. 5A. The waveform of the applied voltage Vm in each case is the sinusoidal waveform shown in FIG. 3B.

When both of the graphs are compared with each other, it is clear that a difference (difference of current values) between the "output current Im when the SOx concentration of the gas to be detected is 0 ppm" represented as a line L1 and the "output current Im when the SOx concentration of the gas to be detected is 130 ppm" represented as a line L2 in a voltage range lower than the decomposition start voltage (0.6 V) of SOx appears more clearly in the example of FIG. 5A than in the example of FIG. 5B. As described above, the sweep speed of the voltage application sweep in the example shown in FIG. 5A is higher than that in the example shown in FIG. 5B. In other words, a current change (reoxidation current change) significant for the SOx concentration detection appears in the example of FIG. 5A. A mechanism for such a phenomenon is considered/inferred as follows.

When the sweep speed is lower than a predetermined speed, the reoxidation reaction of S progresses continuously and gradually during the voltage decrease sweep, and thus, a significant reoxidation current change does not appear. In contrast, when the sweep speed is higher than the predetermined sweep speed, it is inferred/considered that the applied voltage Vm decreases before the reoxidation reaction of S has sufficiently progressed during the voltage decrease sweep, and when the applied voltage Vm becomes a voltage in a "certain voltage range in which the reoxidation reaction of S is very active", the reoxidation reaction of S drastically/rapidly progresses. As a result, the significant current change for the SOx concentration detection appears.

As described above, whether or not the current change which is significant and useful for the SOx concentration detection appears depends on the sweep speed when the voltage decrease sweep is performed. Thus, the sweep speed of the voltage decrease sweep needs to be such a predetermined speed that can cause the significant current change representing the reoxidation current change to appear.

This predetermined speed is set to an appropriate speed at which the significant current change representing the reoxidation current change occurs, the appropriate speed being determined through experiments performed in advance for the first detection device.

According to the experiments, when the voltage in the sinusoidal waveform shown in FIG. 3B is applied between the first electrode 41a and the second electrode 41b, it has become clear that the sweep speed may be set in such a manner that a frequency F of the waveform is within a predetermined range (typically, a range equal to or higher than 0.1 Hz and equal to or lower than 5 Hz (0.1 Hz≤F≤5 Hz)). A lower limit value of the frequency F in the predetermined range is determined from a viewpoint that a significant signal difference (significant reoxidation current change) for the SOx concentration detection is no longer acquired when the frequency F has a value lower than the lower limit value. An upper limit value of the frequency F in the predetermined range is determined from a viewpoint that an influence of current change factors (specifically, a capacitance of the solid electrolyte body 41s, and the like) other than the SOx concentration becomes excessively large when the frequency F has a value higher than the upper limit value.

Figure 3C:
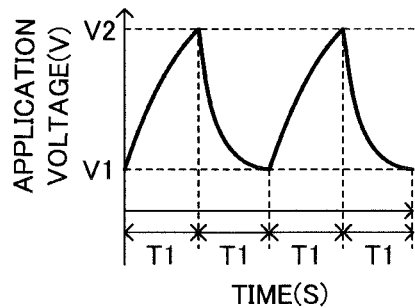
FIG. 3C is a graph for showing another waveform of the applied voltage exhibited when the SOx detection is performed.

Further, according to the experiments in which the voltage having the non-sinusoidal waveform observed when a capacitor is charged and discharged as shown in FIG. 3C is applied between the first electrode 41a and the second electrode 41b, it has become clear that the sweep speed may be set to a sweep speed that has a response time constant T1 of the voltage switching waveform be in a predetermined range (typically, a range equal to or more than 0.1 second and equal to or less than 5 seconds, namely 0.1 s≤T1≤5 s). The response time constant T1 is a period required for the applied voltage Vm to change from the lower limit voltage (first voltage) of the predetermined range to the upper limit voltage (second voltage) of the predetermined range, or to change in an opposite direction in the predetermined range.

When the predetermined range of the frequency F and the response time constant T1 are converted into periods required for the voltage decrease sweep (namely, a period required for the supplied voltage Vm to reach the first voltage V1 from the second voltage V2), a range of each of the periods is equal to or longer than 0.1 second and equal to or shorter than 5 seconds (0.1 s≤the period≤5 s). Thus, this period may be in a range equal to or more than 0.1 second and equal to or less than 5 seconds.

Further, it has become clear that the "reoxidation current change" highly depends mainly on the S concentration in the exhaust gas (gas to be detected) as described later with reference to FIG. 6A and FIG. 6B. In other words, the reoxidation current change is unlikely to be influenced by "gas (e.g., water) of the oxygen-containing components other than the sulfur oxide (SOx)" in the exhaust gas. That is, when the voltage increase sweep is performed, decomposition products (for example, hydrogen which is a decomposition product of water) of the "oxygen-containing components other than the sulfur oxide" are not adsorbed to the first electrode 41a. Therefore, a phenomenon that the decomposition products of the "oxygen-containing components other than the sulfur oxide" return to the oxygen-containing components through the reoxidation reaction on the first electrode 41a does not substantially occur during the voltage decrease sweep. As a result, the SOx concentration in the exhaust gas can accurately be detected through use of the reoxidation current change.

Figure 6A:
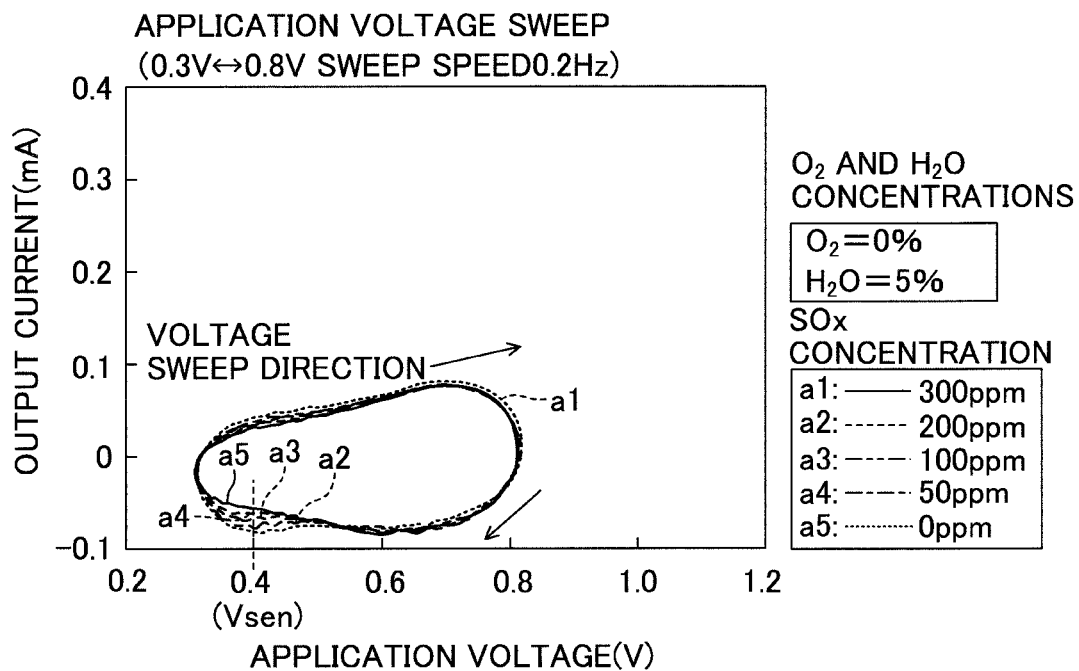
FIG. 6A is a graph for showing a relationship between the applied voltage and the output current exhibited when a SOx concentration of exhaust gas (gas to be detected) is variously changed.

FIG. 6A is a graph for schematically showing relationships between the applied voltage (applied voltage having the sinusoidal waveform) Vm and the output current Im when the applied voltage sweep is performed for various concentrations of SOx contained in the exhaust gas (gas to be detected) while keeping the applied voltage range and the sweep speed unchanged. According to the examples shown in FIG. 6A, it can be confirmed that the output current Im (reoxidation current Is) at a reoxidation current detection voltage Vsen (=0.4 V) described later decreases as the concentration of the SOx in the exhaust gas increases.

Figure 6B:
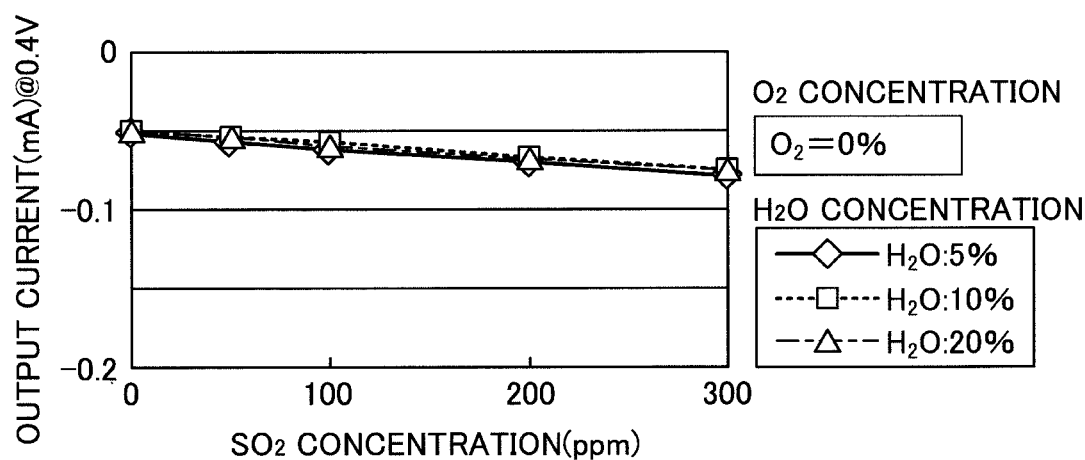
FIG. 6B is a graph for showing a relationship between the output current and the SOx ($SO_2$) concentration exhibited when an $H_2O$ concentration of the exhaust gas (gas to be detected) is variously changed.

FIG. 6B is a graph for showing relationships between the SOx concentration ($SO_2$ concentration) and the output current Im (reoxidation current Is) at the reoxidation current detection voltage Vsen when the applied voltage sweep is performed under the same condition as that in the examples shown in FIG. 6A while changing the concentration of $H_2O$ contained in the exhaust gas (gas to be detected) to various values. According to the example shown in FIG. 6B, it can be confirmed that the output current Im (reoxidation current Is) at the reoxidation current detection voltage Vsen (=0.4 V) varies depending on the SOx concentration in the exhaust gas, but does not vary depending on the concentration of $H_2O$ in the exhaust gas. From the above, it is understood that the concentration of SOx in the exhaust gas can accurately/precisely be detected through use of the reoxidation current change without being influenced by the "oxygen-containing components (e.g., water) other than SOx" in the exhaust gas. Thus, the first detection device is configured to use this reoxidation current change to detect the SOx concentration (in actuality, absence/presence of the SOx having the concentration equal to or higher than the predetermined concentration).

[Parameter for Detecting Reoxidation Current Change]

The first detection device is configured to acquire a parameter appropriately (accurately) representing a "degree of the reoxidation current change", and detect the SOx concentration based on the acquired parameter. More specifically, the first detection device acquires the output current Im (hereinafter referred to as a "reoxidation current Is") when the applied voltage Vm becomes equal to the "above-mentioned reoxidation current detection voltage Vsen selected from the first voltage range (less than the decomposition start voltage of SOx)" during the voltage decrease sweep. Further, the first detection device acquires a base current Ibas described later. Thereafter, the first detection device acquires a difference Id (=Ibas−Is) between the base current Ibas and the reoxidation current Is as the "parameter (appropriately/accurately) representing the degree of the reoxidation current change".

The base current Ibas is the output current Im at the reoxidation current detection voltage Vsen when exhaust gas which does not containing S is made to flow through the exhaust passage in advance, and the applied voltage sweep is performed under the same condition (with the same waveform, the same voltage range, and the same sweep speed) as that in a case in which the SOx concentration in the exhaust gas is actually detected. The reoxidation current Is may be an average reoxidation current Iave acquired by averaging a plurality of the "output currents Im at the reoxidation current detection voltage Vsen" acquired by performing the applied voltage sweep for a plurality of times. The first detection device performs the SOx concentration detection based on the above parameter (difference Id).

[SOx Concentration Detection Method]

The first detection device is configured to use the above-mentioned detection principle for the SOx concentration to perform the SOx concentration detection as follows.

The first detection device performs the applied voltage sweep at the "predetermined sweep speed" at which the significant reoxidation current change appears as described above. In this case, a particularly important point is the voltage decrease sweep speed (sweep speed of the voltage decrease sweep). Note that the first detection device determines the voltage range of the applied voltage sweep based on the air-fuel ratio A/F of the engine detected based on the oxygen concentration in the exhaust gas.

The first detection device acquires/detects the output current Im at the reoxidation current detection voltage Vsen during the voltage decrease sweep as the reoxidation current Is.

The first detection device calculates the difference Id (=Ibas−Is) between the base current Ibas and the reoxidation current Is.

The first detection device determines whether or not the SOx having the predetermined concentration or higher is contained based on the difference Id. The difference Id has a value equal to or larger than 0, and is thus equal to the magnitude of the difference Id.

Specifically, the first detection device applies the voltage having the voltage waveform of the sinusoidal wave shown in FIG. 3B between the first electrode 41a and the second electrode 41b when the SOx concentration detection is performed. In this instance, the first detection device performs the applied voltage sweep (voltage increase sweep and the voltage decrease sweep) in the predetermined voltage range at the above-mentioned sweep speed (frequency in the above-mentioned frequency range) at which the above-mentioned current change significant for the SOx concentration detection appears/occurs.

Figure 7:
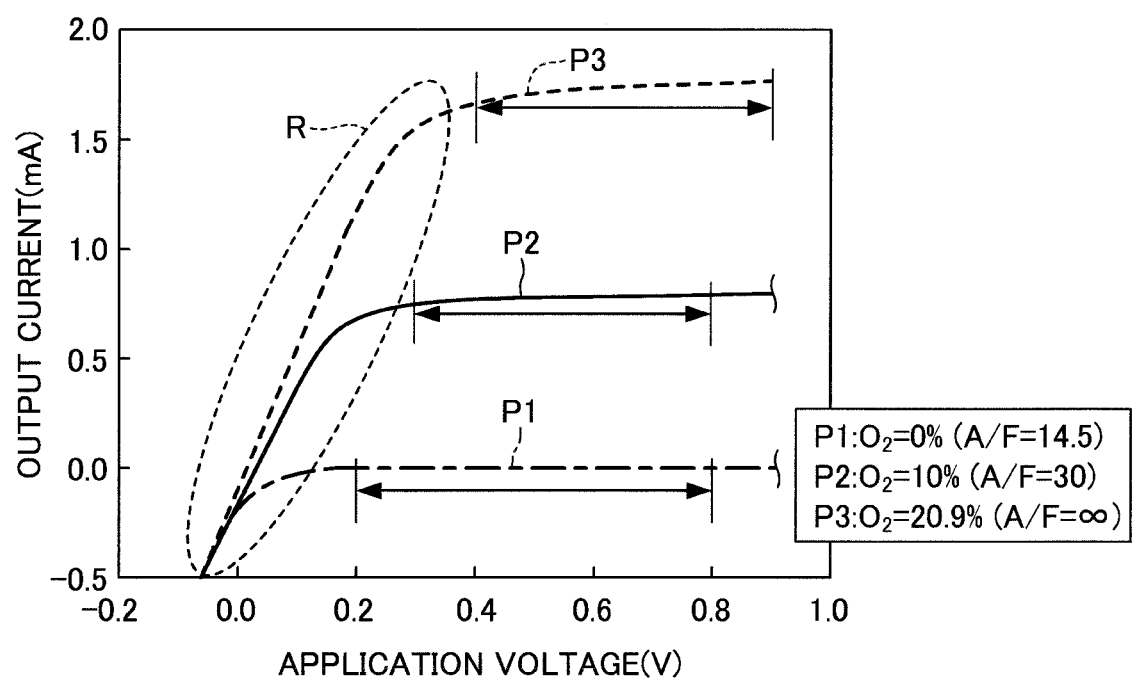
FIG. 7 is a graph for showing a relationship between an air-fuel ratio A/F of mixture in a combustion chamber and a limiting current region of the oxygen.

More specifically, the first detection device determines the voltage range of the applied voltage sweep (the upper limit voltage and the lower limit voltage of the sweep of the applied voltage) based on the air-fuel ratio A/F of the engine. As shown in FIG. 7, the lower limit voltage of the applied voltage sweep is set so as to avoid detecting the output current Im which is in an internal resistance dependent region surrounded by a dotted line R, and is set to be a voltage higher than the minimum value of the voltage for the limiting current region of the oxygen. The internal resistance dependent region is a region in which the output current Im increases as the applied voltage Vm increases. The upper limit voltage of the applied voltage Vm in the internal resistance dependent region increases as the air-fuel ratio A/F of the engine becomes leaner/larger (i.e., as the oxygen concentration in the exhaust gas increases). The upper limit voltage of the applied voltage sweep may be constant, but is set so as to increase as the lower limit voltage of the applied voltage sweep increases. Hereinafter, the lower limit voltage of the voltage range of the applied voltage sweep is also referred to as a "lower limit voltage (first voltage V1) of the applied voltage sweep".

Specifically, the upper limit value of the applied voltage Vm in the internal resistance dependent region R increases as the air-fuel ratio A/F of the engine becomes larger/leaner. Thus, the first detection device is configured to increase the lower limit voltage (first voltage V1) of the applied voltage sweep as the air-fuel ratio A/F of the engine becomes larger/leaner so that the voltage range of the applied voltage sweep does not enter/overlap the internal resistance dependent region R.

According to the experiments performed by the inventor(s) of the present application, when the A/F is 14.5 (stoichiometric), the first voltage V1 may be a value selected from a range equal to or higher than 0.2 V, and the first detection device thus sets the first voltage V1 to 0.2 V. When the A/F is 30, the first voltage V1 may be a value selected from a range equal to or higher than 0.3 V, and the first detection device thus sets the first voltage V1 to 0.35 V.

As described above, when the voltage increase sweep and the voltage decrease sweep are performed, and if SOx is contained in the exhaust gas, S (sulfur) generated as a result of the decomposition of SOx during the voltage increase sweep is adsorbed to the first electrode 41a. S adsorbed to the first electrode 41a is reoxidized (oxidized again) during the voltage decrease sweep.

Figure 8:
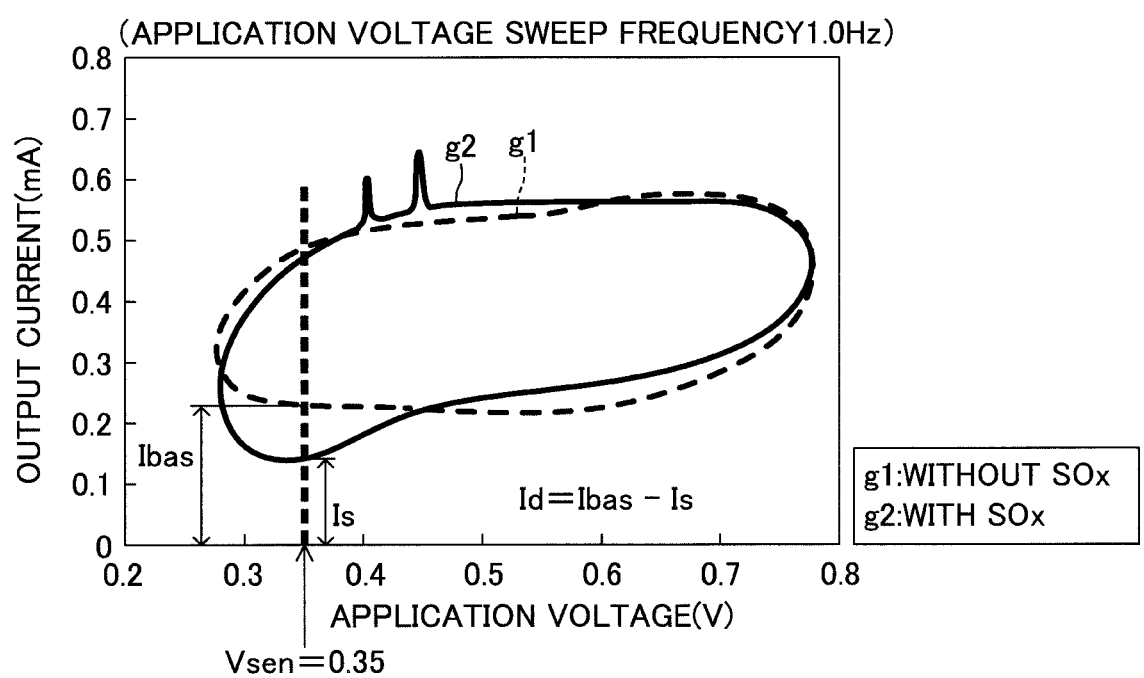
FIG. 8 is a graph for showing an example of a relationship between the applied voltage and the output current exhibited when an applied voltage sweep is performed.

The first detection device is configured to use the above-mentioned parameter (=difference Id) to detect the reoxidation current change, to thereby detect the SOx concentration. In other words, the first detection device is configured to acquire the output current Im (as the base current Ibas) at the reoxidation detection voltage Vsen during the voltage decrease sweep using the output current Im illustrated by a line g1 of FIG. 8, and store this base current Ibas in the ROM in advance. Further, the first detection device is configured to perform the applied voltage sweep, to thereby acquire the output current Im (as the reoxidation current Is) at the reoxidation detection voltage Vsen during the voltage decrease sweep using the output current Im illustrated by a line g2 of FIG. 8. Furthermore, the first detection device is configured to acquire the difference Id (=Ibas−Is: parameter representing the degree of the reoxidation current change) between the base current Ibas and the reoxidation current Is. The first detection device is configured to detect the SOx concentration (determine absence/presence of the SOx having the concentration equal to or higher than the predetermined concentration in the exhaust gas) based on the difference Id (magnitude of the difference Id).

<Outline of Element Temperature Control of Gas Sensor>

As illustrated in FIG. 3A, at the time point t0 at which the internal combustion engine 10 is started, the first detection device starts the energization control to control the electric power supplied to the heater 71 so that the solid electrolyte body 41s is heated by the heater 71. Specifically, the first detection device is configured to perform the energization control of the heater 71 through (target) impedance feedback control.

Figure 9:
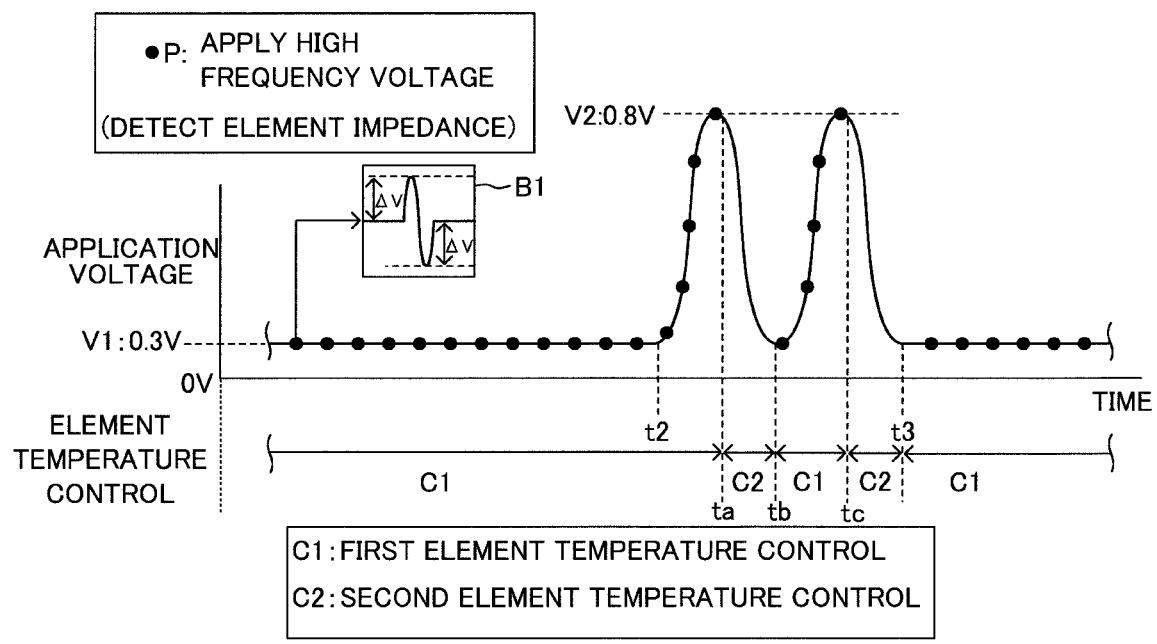
FIG. 9 is a time chart for explaining an overview of the element temperature control operation performed by a CPU of an ECU of the gas detection device according to the first embodiment of the present disclosure.

That is, the first detection device is configured to calculate an impedance (element impedance) of the element part 40 based on the electrode current Im detected when a predetermined high frequency voltage (for example, a high frequency voltage whose frequency is within a range from several kHz to 10 kHz) is applied between the first electrode 41a and the second electrode 41b, at time points P shown in FIG. 9. Specifically, as illustrated in block 81 of FIG. 9, the first detection device varies the applied voltage by ΔV (raising and lowering the applied voltage by ΔV) from the applied voltage immediately before applying the high frequency voltage to acquire the change amount ΔI of the output current when the applied voltage is changed by ΔV. The first detection device calculates the element impedance by dividing ΔV by ΔI (element impedance=ΔV/ΔI).

The first detection device is configured to control the electric power supplied to the heater 71 in such a manner that the element impedance acquired as temperature Information matches (becomes equal to) a target impedance set in advance (see, for example, Japanese Patent Application Laid-open Publication No. 2002-71633 and Japanese Patent Application Laid-open Publication No. 2009-53108).

In the present specification, the process for detecting the element impedance described above may be referred to as an "element impedance detection process". Further, an element temperature control for performing the "element impedance detection process" and controlling the electric power supplied to the heater 71 in such a manner that the detected element impedance becomes equal to the target impedance set in advance may sometimes be referred to as a "first element temperature control".

The first element temperature control will be more specifically described as follows. The first detection device detects the element impedance by performing the "element impedance detection process". When the detected element impedance is larger than the target impedance corresponding to the target temperature set in advance, the element temperature at the detection time point is lower than the target temperature. Therefore, in this case, the first detection device increases an energization control amount (more specifically, the duty ratio) to the heater 71 to increase a heating amount for the element part 40 per unit time (the amount of the electric power supplied to the heater 71), to thereby control the element temperature so that the element temperature comes closer to the target temperature.

In contrast, when the detected element impedance is smaller than the target impedance corresponding to the target temperature set in advance, the element temperature at the detection time point is higher than the target temperature. Therefore, in this case, the first detection device decreases the energization control amount (the duty ratio) to the heater 71 to decrease the heating amount for the element part 40 per unit time (the amount of the electric power supplied to the heater 71), to thereby control the element temperature so that the element temperature comes closer to the target temperature.

As a result, the solid electrolyte body 41s is heated to the predetermined temperature equal to or higher than the temperature (the activation temperature) at which oxide ion conductivity appears. In this manner, the element part 40 is maintained at the predetermined temperature (the target temperature).

However, since the "element impedance detection process" is a process to cause the output current to be changed, the output current inevitably varies while the element impedance detection process is being performed. Therefore, it is difficult for the first detection device to acquire the reoxidation current Is accurately representing the reoxidation current change while the element impedance detection process is being performed.

Further, when the "element impedance detection process" is performed during the applied voltage sweep (especially during the voltage decrease sweep), the high frequency voltage influences the SOx reaction (e.g., decomposition of SOx, SOx adsorption to the electrode, and SOx desorption from the electrode), resulting in fluctuation in the output current (which may additionally be caused by noises and the like). As a result, the accuracy in detecting the SOx concentration is likely to be degraded.

In view of the above, the first detection device is configured to stop the "element impedance detection process" in a period in which the first detection device performs the voltage decrease sweep (a period including the timing of acquiring the reoxidation current Is) (i.e., a period from a time point ta to a time point tb and a period from a time point tc to the time point t3) during performing the applied voltage control for SOx detection (a period from a time point t2 to immediately before a time point t3).

Thereby, the "element impedance detection process" is prevented from being performed when the reoxidation current Is is acquired, so that the reoxidation current Is accurately representing the reoxidation current change can be acquired. Further, the "element impedance detection process" is prevented from being performed while the voltage decrease sweep is being performed, so that the influence of the applied high frequency voltage on the SOx reaction can be lowered. As a result of those, the first detection device can accurately detect the SOx concentration.

Further, while the first detection device stops the "element impedance detection process", the first detection device keeps the element impedance at the impedance which was detected a predetermined time before the detection process was stopped (specifically, immediately before the detection process is stopped) and controls the energization for the heater 71 so as to maintain the electric power supplied to the heater 71 at a predetermined electric power in order to control the element temperature. Specifically, the first detection device maintains the energization control amount (the duty ratio) to the heater 71 which was set a predetermined time before the detection process was stopped so as to maintain the electric power supplied to the heater 71 at a certain value. It should be noted that such an element temperature control may sometimes be referred to as a "second element temperature control". The first detection device may control the electric power supplied to the heater 71 by maintaining a preset energization control amount (duty ratio) in such a manner that an amount of predetermined electric power which is set in advance is supplied to the heater 71 while "the element impedance detection process" is stopped".

The period during which the applied voltage control for SOx detection is performed is not so long and is a period in which the operating conditions are in a stable state. Therefore, even if the "second element temperature control" is performed for the period during which the voltage decrease sweep is performed, the element temperature is maintained at a temperature suitable for the SOx detection and is unlikely to change by an amount which would affect the accuracy of SOx concentration detection.

<Specific Operation>

A description is now given of a specific operation of the first detection device. The CPU (hereinafter simply referred to as a "CPU") of the ECU 20 is configured to execute each of routines illustrated by flowcharts of FIGS. 10 to 12 every time a predetermined period elapses, using the gas sensor 30.

A value of each of flags described below and used in those routines is set to "0" in an initial routine executed by the CPU when a position of an ignition key switch (not shown) installed on the vehicle is changed from an off position to an on position.

Sensor activeness flag Xact: a sensor activeness flag Xact represents that the gas sensor 30 is in an "active state" when its value is "1". The sensor activeness flag Xact represents that the gas sensor 30 is not in the "active state" (in a sensor inactive state) when its value is "0".

Current acquisition completion flag Xa: a current acquisition completion flag Xa represents that, at the current time point, the acquisition of the "reoxidation current Is" which is necessary to calculate the difference Id has been completed when its value is "1". The current acquisition completion flag Xa represents that, at the current time point, the acquisition of the "reoxidation current Is" has not been completed when its value is "0".

Applied voltage sweep execution flag Xsw: an applied voltage sweep execution flag Xsw represents that the applied voltage sweep (applied voltage control for the SOx detection) is being performed at the current time point when its value is "1". The applied voltage sweep execution flag Xsw represents that the applied voltage sweep is not being performed at the current time point when its value is "0".

SOx concentration detection completion flag XSOx: a SOx concentration detection completion flag XSOx represents that, at the current time point, the SOx concentration detection has been completed when its value is "1". The SOx concentration detection completion flag XSOx represents that, at the current time point, the SOx concentration detection has not been completed when its value is "0".

Figure 10:
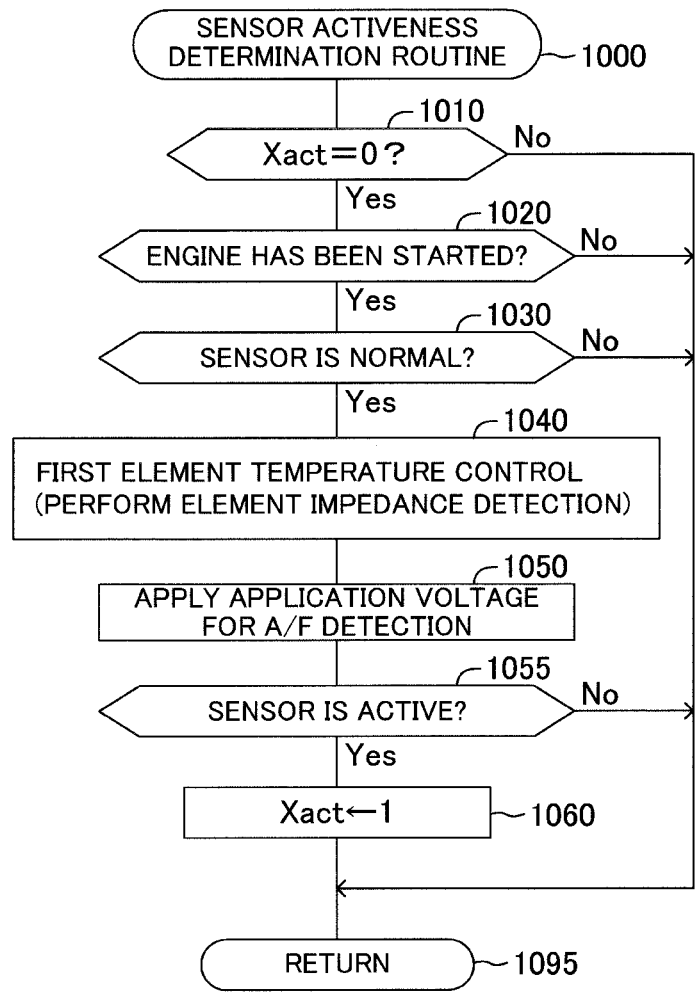
FIG. 10 is a flowchart for illustrating a sensor activity determination routine executed by the CPU of the ECU illustrated in FIG. 1.

The CPU starts processing from step 1000 of a sensor activeness determination routine illustrated in FIG. 10 at a predetermined timing, and proceeds to step 1010 to determine whether or not the value of the sensor activeness flag Xact is "0".

When the current time point is immediately after the position of the ignition key switch has been changed to the on position, the value of the sensor activeness flag Xact is "0". In this case, the CPU makes a "Yes" determination at step 1010 and proceeds to step 1020 to determine whether or not the engine has been started (the internal combustion engine 10 has been started).

If the engine has been started, the CPU makes a "Yes" determination at step 1020 and proceeds to step 1030 to determine whether or not the gas sensor 30 is normal through a widely known method. For example, in a previous operation of the internal combustion engine 10, if the output current Im did not change when the operation state of the internal combustion engine 10 changed from a fuel injection state to a fuel cut state while the A/F was being detected (that is, while the applied voltage Vm was being set at the voltage Vaf for the oxygen concentration detection), the CPU determined that the gas sensor 30 was abnormal, and stored this event in a backup RAM that can hold stored contents even when the ignition key switch is off. The CPU determines whether or not the gas sensor 30 is normal based on the stored content in the backup RAM at step 1030 of the present routine.

When the gas sensor 30 is normal, the CPU makes a "Yes" determination at step 1030 to sequentially performs step 1040 and step 1050, and then proceeds to step 1055.

Step 1040: the CPU performs the first element temperature control. In other words, the CPU performs the element impedance detection process and controls the electric power supplied to the heater 71 in such a manner that the detected element impedance matches the preset target impedance.

Step 1050: the CPU applies the applied voltage Vaf (specifically, 0.3 V) for the oxygen concentration detection (in other words, for the A/F detection) between the first electrode 41a and the second electrode 41b. In other words, the CPU sets the applied voltage Vm to the applied voltage Vaf for the oxygen concentration detection.

The CPU proceeds to step 1055 to determine whether or not the gas sensor 30 is active (sensor-active). Specifically, the CPU determines whether or not the element impedance acquired at step 1040 has a value smaller than a sensor activeness determination value. When the gas sensor 30 is not sensor-active, the CPU makes a "No" determination at step 1055 and proceeds to step 1095 to tentatively terminate the present routine.

In contrast, when the gas sensor 30 is sensor-active (when the element impedance acquired at step 1040 has a value smaller than the sensor activeness determination value), the CPU makes a "Yes" determination at step 1055 and proceeds to step 1060 to set the value of the sensor activeness flag Xact to "1". Thereafter, the CPU proceeds to step 1095 to tentatively terminate the present routine.

When the value of the sensor activeness flag Xact is not "0" at a time point when the CPU executes the process of step 1010, the CPU makes a "No" determination at step 1010 and proceeds to step 1095 to tentatively terminate the present routine. Further, when the engine has not started at a time point when the CPU executes the process of step 1020, the CPU makes a "No" determination at step 1020 and proceeds to step 1095 to tentatively terminate the present routine. Furthermore, when the gas sensor 30 is not normal at a time point when the CPU executes the process of step 1030, the CPU makes a "No" determination at step 1030 and proceeds to step 1095 to tentatively terminate the present routine.

Figure 11:
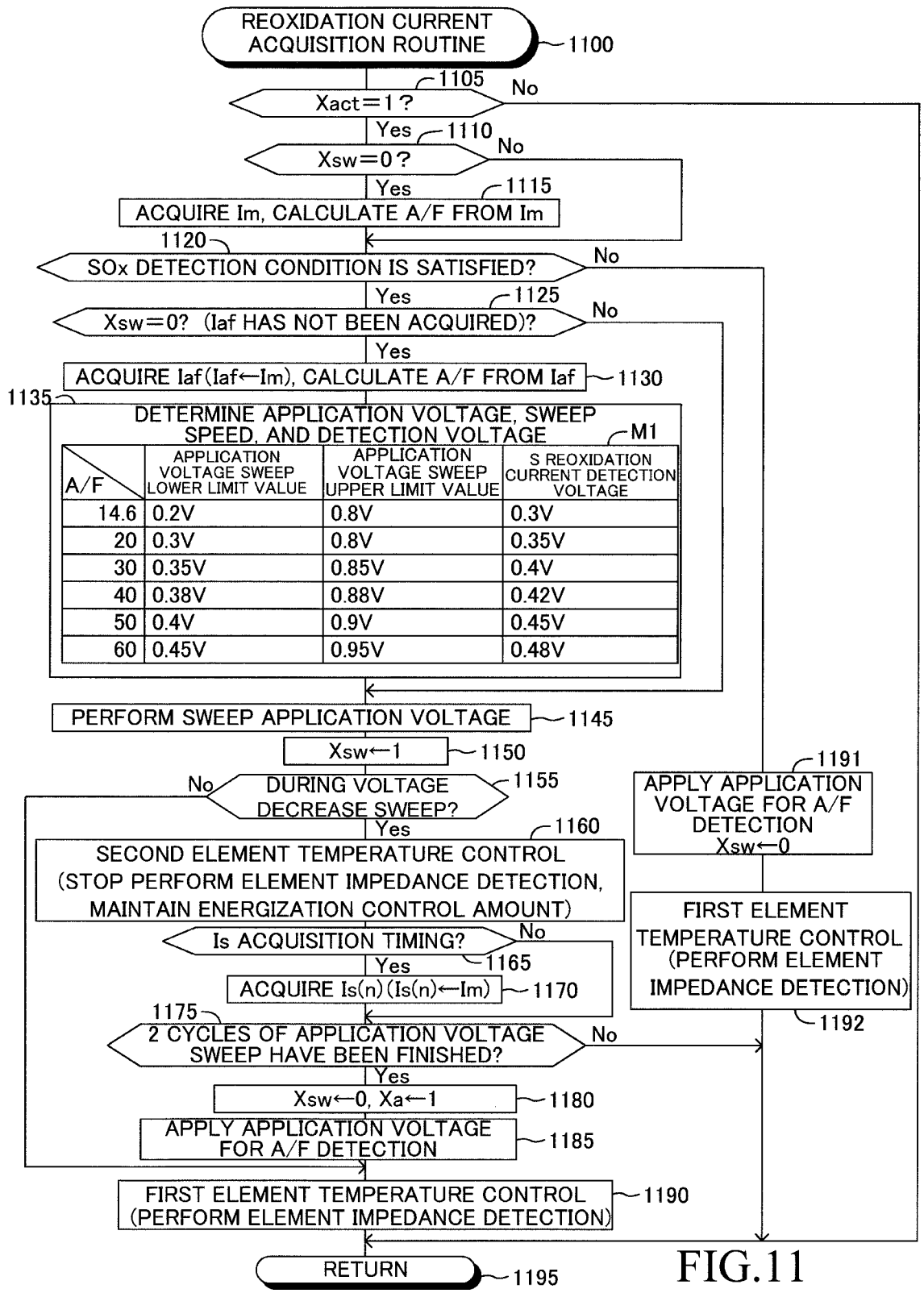
FIG. 11 is a flowchart for illustrating a reoxidation current acquisition routine executed by the CPU of the ECU illustrated in FIG. 1.

With reference to FIG. 11, a description is now given of a reoxidation current acquisition routine. The CPU starts processing from step 1100 of FIG. 11 at a predetermined timing, and proceeds to step 1105 to determine whether or not the value of the sensor activeness flag Xact is "1".

The reoxidation current acquisition routine substantially functions after the gas sensor 30 becomes sensor-active so that the value of the sensor activeness flag Xact is set to "1".

Thus, when the value of the sensor activeness flag Xact is not "1" (in other words, when the value of the sensor activeness flag Xact is "0"), the CPU makes a "No" determination at step 1105 and proceeds to step 1195 to tentatively terminate the present routine.

In contrast, when the value of the sensor activeness flag Xact is set to "1" through executing step 1060 in FIG. 10, the CPU makes a "Yes" determination at step 1105 and proceeds to step 1110 to determine whether or not the value of the applied voltage sweep execution flag Xsw representing whether or not the applied voltage sweep is being performed is "0".

When the value of the applied voltage sweep execution flag Xsw is 0, the CPU makes a "Yes" determination at step 1110 to proceeds to step 1115, at which the CPU detects the oxygen concentration based on the output current Im acquired from the gas sensor 30, and applies the oxygen concentration to a predetermined lookup table (also referred to as a "map") to calculate/obtain the air-fuel ratio A/F of the engine. Thereafter, the CPU proceeds to step 1120. When the time point at which the process of step 1110 is executed is after the start of the execution of the applied voltage sweep, and thus, the value of the applied voltage sweep execution flag Xsw is "1" (refer to step 1150 described later), the CPU makes a "No" determination at step 1110 to directly proceed to step 1120.

When the CPU proceeds to step 1120, the CPU determines whether or not all of the following conditions constituting SOx detection condition are satisfied based on the information acquired from various sensors (for example, the NE sensor 21, the water temperature sensor 22). When all of the following conditions are satisfied, the SOx detection condition is satisfied.

<<SOx Detection Condition>>

The internal combustion engine 10 is in a state after it is warmed up (in other words, the coolant temperature THW is equal to or higher than a warming up completion water temperature THWth).

The gas sensor 30 is sensor-active.

The state is not the fuel cut state.

The air-fuel ratio A/F of the engine is stable. In other words, the operation state of the Internal combustion engine 10 is in an idling state, or the operation state of the vehicle is a steady travelling state. Whether or not the operation state of the internal combustion engine 10 is in the idling state is determined by determining whether or not a "state in which the accelerator pedal operation amount AP is '0', and the engine rotation speed NE is equal to or lower than a predetermined rotation speed" has continued for a time equal to or longer than a predetermined idling time. Whether or not the operation state of the vehicle is in the steady travelling state is determined by determining whether or not a "state in which a change amount per unit period in the accelerator pedal operation amount AP is equal to or smaller than a threshold operation change amount, and a change amount in the speed of the vehicle per unit period is equal to or smaller than a threshold vehicle speed change amount" has continued for a time equal to or longer than a predetermined steady travelling threshold time.

The SOx concentration detection has not been performed yet (the value of the SOx concentration detection completion flag XSOx is not "1") before the position of the ignition key switch is changed to the off position after it was changed from the off position to the on position (in other words, after the start of the current operation of the internal combustion engine 10).

When the SOx detection condition is satisfied, the CPU makes a "Yes" determination at step 1120 and proceeds to step 1125 to determine whether or not the value of the applied voltage sweep execution flag Xsw is "0". As described later, when the value of the applied voltage sweep execution flag Xsw is "1", the output current Iaf (used for the A/F detection) immediately before the applied voltage sweep is started has already been acquired (refer to step 1130 and step 1150). Thus, when the value of the applied voltage sweep execution flag Xsw is "0", the output current Iaf immediately before the applied voltage sweep is started has not been acquired yet.

Thus, when the value of the applied voltage sweep execution flag Xsw is "0", the CPU makes a "Yes" determination at step 1125 to proceed to step 1130, at which the CPU acquires the output current Im at this time point as the output current Iaf (output current Im when the applied voltage Vm is equal to the voltage Vaf for the oxygen concentration detection), detects the oxygen concentration based on the acquired output current Iaf, and applies the oxygen concentration to the predetermined lookup table, to thereby calculate/obtain the air-fuel ratio A/F of the engine.

Thereafter, the CPU proceeds to step 1135 to apply the air-fuel ratio A/F calculated based on the acquired output current Iaf to a lookup table M1 to thereby determine the sweep voltage range (the lower limit voltage (first voltage V1) and the upper limit voltage (second voltage V2)) of the applied voltage sweep, and the reoxidation current detection voltage Vsen. Then, the CPU proceeds to step 1145.

In contrast, when the value of the applied voltage sweep execution flag Xsw is not "0" at the time point when the CPU executes the process of step 1125, the CPU makes a "No" determination at step 1125, and directly proceeds to step 1145.

When the CPU proceeds to step 1145, the CPU performs the applied voltage sweep having the sweep voltage range determined at step 1135 at the predetermined applied voltage sweep speed (one cycle=1 second). In other words, the CPU executes processes for applying the voltage having the sinusoidal wave for two cycles under the sweep conditions (the voltage range, and the sweep speed). When the applied voltage sweep has already been started and being performed at the time point of step 1145 (when the CPU has made a "No" determination at step 1125), the CPU continues the execution of the applied voltage sweep.

Thereafter, the CPU proceeds to step 1150 to set the value of the applied voltage sweep execution flag Xsw to "1". Subsequently, the CPU proceeds to step 1155 to determine whether or not the current time point is within the voltage decrease sweep of each cycle out of the two cycles of the voltage application sweep.

When the current time point is not within the voltage decrease sweep (that is, the voltage increase sweep is being performed), the CPU makes a "No" determination at step 1155 and proceeds to step 1190 to perform the first element temperature control. If the first element temperature control has already been started to be performed at a time point at which the CPU executes the process of step 1155, the CPU continues its first element temperature control. In contrast, if the second element temperature control has already been started to be performed at a time point at which the CPU executes the process of step 1155, the CPU stops the second element temperature control to perform the first element temperature control. Then, the CPU proceeds to step 1195 to tentatively terminate the present routine.

When the current time point is within/during the voltage decrease sweep, the CPU makes a "Yes" determination at step 1155 and proceeds to step 1160 to perform the second element temperature control. In other words, the CPU stops the element impedance detection process, and holds the element impedance detected immediately before the element impedance detection process is stopped. Further, the CPU maintains the energization control amount (duty ratio) for the heater 71 which has been set/determined based on the held element impedance immediately before the element impedance detection process is stopped, to thereby control the electric power supplied to the heater 71 in such a manner that the electric power is maintained at the same power as that supplied to the heater 71 immediately before the element impedance detection process is stopped.

When the second element temperature control has already been started to be performed at a time point at which the CPU executes the process of step 1160, the CPU continues its second element temperature control. When the first element temperature control has already been started to be performed at a time point at which the CPU executes the process of step 1160, the CPU stops the first element temperature control to perform the second element temperature control.

Then, the CPU proceeds to step 1165, and determines whether or not the current time point is acquisition timing for the reoxidation current Is. Specifically, the CPU determines whether or not the current time point is within/during the voltage decrease sweep of each cycle out of the two cycles of the voltage application sweep, and the applied voltage Vm matches/becomes equal to/reaches the reoxidation current detection voltage Vsen. When the current time point is the acquisition timing for the reoxidation current Is, the CPU makes a "Yes" determination at step 1165 and proceeds to step 1170 to acquire the output current Im at this time point as a reoxidation current Is(n), and store the reoxidation current Is(n) in the RAM. Then, the CPU proceeds to step 1175.

In contrast, at the time point when the CPU executes the process of step 1165, if that time point is not the acquisition timing for the reoxidation current Is, the CPU makes a "No" determination at step 1165 to directly proceed to step 1175.

When the CPU proceeds to step 1175, the CPU determines whether or not the two cycles of the applied voltage sweep have been finished.

When the two cycles of the applied voltage sweep have not been finished, the CPU makes a "No" determination at step 1175 and directly proceeds to step 1195 to tentatively terminate the present routine. In contrast, when the two cycles of the applied voltage sweep have been finished, the CPU makes a "Yes" determination at step 1175; sequentially executes each of processes of step 1180 and step 1185 described later; and then proceeds to step 1190 to execute the process of the above-described step 1190. Then, the CPU proceeds to step 1195 to tentatively terminate the present routine.

Step 1180: the CPU sets (clears) the value of the applied voltage sweep execution flag Xsw to "0", and simultaneously sets the value of the current acquisition completion flag Xa to "1".

Step 1185: the CPU sets the applied voltage Vm to the applied voltage Vaf for the oxygen concentration detection.

When the SOx detection condition is not satisfied at a time point at which the CPU executes the process of step 1120, the CPU makes a "No" determination at step 1120 and proceeds to step 1191 to set the applied voltage Vm to the applied voltage Vaf for the oxygen concentration detection, and set (clears) the value of the applied voltage sweep execution flag Xsw to "0". Thereafter, the CPU proceeds to step 1192 to perform the first element temperature control. When the CPU has already been performing the first element temperature control at the time point at which the CPU executes the process of step 1192, the CPU continues its first element temperature control. When the CPU has already been performing the second element temperature control at the time point at which the CPU executes the process of step 1192, the CPU stops the second element temperature control to perform the first element temperature control. Then, the CPU proceeds to step 1195 to tentatively terminate the present routine.

Through executing the routine shown in FIG. 11, the reoxidation currents Is(1) and Is(2) of the respective cycles of the two cycles of the applied voltage sweep are acquired, and stored in the RAM.

Figure 12:
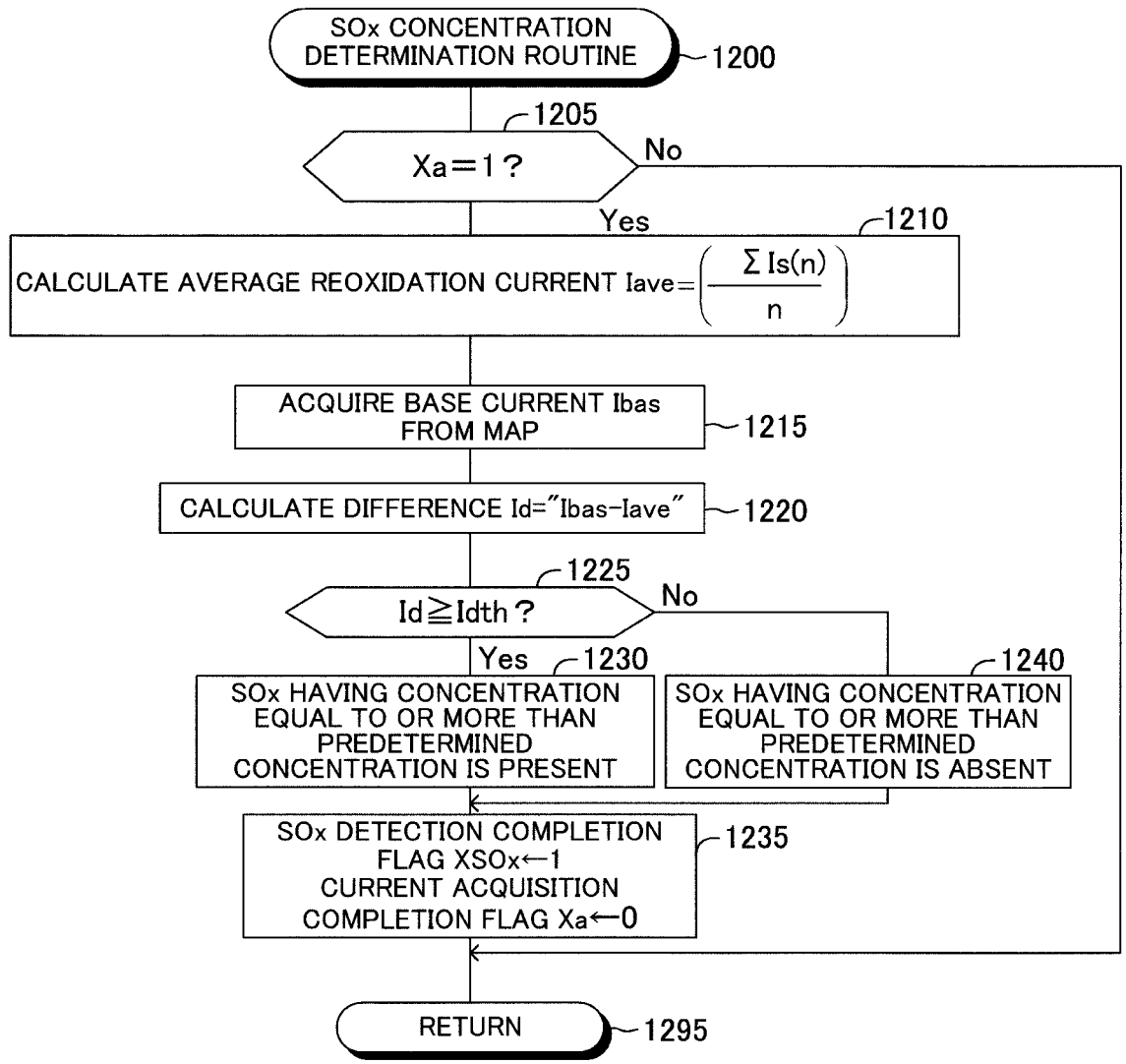
FIG. 12 is a flowchart for illustrating a SOx concentration determination routine executed by the CPU of the ECU illustrated in FIG. 1.

With reference to FIG. 12, a description is now given of a SOx concentration determination routine. The CPU starts processing from step 1200 of FIG. 12 at a predetermined timing, and proceeds to step 1205 to determine whether or not the value of the current acquisition completion flag Xa is "1".

The SOx concentration determination routine substantially functions when the value of the current acquisition completion flag Xa is "1". Thus, when the value of the current acquisition completion flag Xa is not "1", the CPU makes a "No" determination at step 1205 and proceeds to step 1295 to tentatively terminate the present routine.

In contrast, when the value of the current acquisition completion flag Xa has been set to "1" by the process of step 1180 shown in FIG. 11, the CPU makes a "Yes" determination at step 1205 to sequentially execute processes from step 1210 to step 1220 described below, and then proceeds to step 1225.

Step 1210: the CPU calculates the average value (average reoxidation current Iave) of the acquired reoxidation currents Is(1) and Is(2).

Step 1215: the CPU applies the sweep voltage range (the lower limit voltage (first voltage V1) and the upper limit voltage (second voltage V2)) of the applied voltage sweep for the current time to a lookup table MapBse (not shown) to thereby acquire the base current Ibas and a threshold difference Idth. In this instance, the CPU may apply the air-fuel ratio A/F of the engine acquired at step 1130 to the lookup table MapBse. As described before, the base current Ibas is the output current Im at the reoxidation current detection voltage Vsen when the applied voltage sweep having the sweep voltage range for the exhaust gas which has the A/F acquired at step 1130 is performed and when the exhaust gas does not contain SOx. The threshold difference Idth has a value appropriate for determining whether or not SOx having a concentration equal to or higher than the predetermined concentration is contained in the exhaust gas, and determined by experiments or the like performed in advance. In other words, the threshold difference Idth is equal to the difference Id (="Ibas–Iave") acquired when sulfur (S) is mixed in the fuel so that the concentration of the sulfur in the fuel is equal to an upper limit concentration in a permissible/allowable range, and the voltage application sweep is performed under the same conditions (conditions for actually detecting the SOx concentration in the exhaust gas) as described above. The same conditions in this case means that the voltage waveform of the applied voltage sweep, the applied voltage range of the applied voltage sweep, the sweep speed of the applied voltage sweep, the air-fuel ratio of the engine, and the like are the same as those used when actually detecting the SOx concentration in the exhaust gas.

Step 1220: the CPU calculates the difference Id="Ibas–Iave" as the SOx detection parameter Id. The difference Id has a value equal to or larger than 0. Thus, the "difference Id" and the "magnitude of the difference Id" are equal to each other.

The CPU proceeds to step 1225 to determine whether or not the calculated difference (SOx detection parameter) Id (thus, the magnitude of the difference Id) is equal to or larger than the threshold difference Idth. When the difference Id is equal to or larger than the threshold difference Idth, the CPU makes a "Yes" determination at step 1225 to proceed to step 1230, at which the CPU determines that SOx having a concentration equal to or higher than the predetermined concentration (upper limit concentration used when the threshold difference Idth was determined in advance) is contained in the exhaust gas. At this time, the CPU may store, into the backup RAM, information which states that SOx having a concentration equal to or higher than the predetermined concentration is contained in the exhaust gas (or information which states that S of an amount exceeding a permissible value is mixed in the fuel), and may turn on a warning lamp. Thereafter, the CPU proceeds to step 1235 to set the value of the SOx detection completion flag XSOx to "1", and to set the value of the current acquisition completion flag Xa to 0. Then, the CPU proceeds to step 1295 to tentatively terminate the present routine.

In contrast, when the SOx detection parameter Id is neither equal nor larger than the threshold difference Idth (in other words, when the SOx detection parameter Id is smaller than the threshold difference Idth), the CPU makes a "No" determination at step 1225 to proceed to step 1240, at which the CPU determines that the SOx having a concentration equal to or higher than the predetermined concentration is not contained in the exhaust gas. At this time, the CPU may store, into the backup RAM, information which states that SOx having a concentration equal to or higher than the predetermined concentration is not contained in the exhaust gas (or information which states that S of an amount exceeding a permissible value is not mixed in the fuel), and may turn off the warning lamp. Then, the CPU proceeds to step 1235 to set the value of the SOx detection completion flag XSOx to "1" and to set the value of the current acquisition completion flag Xa to 0. Then, the CPU proceeds to step 1295 to tentatively terminate the present routine.

As described above, when the first detection device performs the voltage decrease sweep during which the reoxidation current Is for detecting the SOx concentration is acquired, the first detection device stops the first element temperature control (element impedance detection process) to perform the second element temperature control.

As a result, since the "element impedance detection process" is not performed at the timing of acquiring the reoxidation current Is, the first detection device can acquire the reoxidation current Is accurately representing the reoxidation current change. Therefore, it is possible to reduce the possibility that the parameter (Id) appropriately indicative of the "degree of reoxidation current change" cannot be acquired due to the "element impedance detection process". Further, since the "element impedance detection process" is not executed while the voltage decrease sweep is being performed, the first detection apparatus can reduce the influence on the SOx reaction caused by applying the high frequency voltage. Further, the first detection device performs the "second element temperature control" only when the voltage decrease sweep is performed. As a result, the first detection device can maintain the element temperature at a temperature suitable for the SOx concentration detection and prevent the element temperature from changing to a degree to affect the accuracy of SOx concentration detection. As a result of these, the first detection device can accurately detect the SOx concentration.

<First Modification>

A description is now given of the gas detection device (hereinafter sometimes referred to as "first modified detection device") according to a first modification example of the present disclosure.

The first detection device is configured to compare the magnitude of the difference Id with the threshold difference Idth to thereby determine whether or not the SOx having a concentration equal to or higher than the predetermined concentration Is contained in the exhaust gas. In contrast, the first modified detection device is configured to acquire the SOx concentration in the exhaust gas based on the difference Id as described below.

Figure 13:
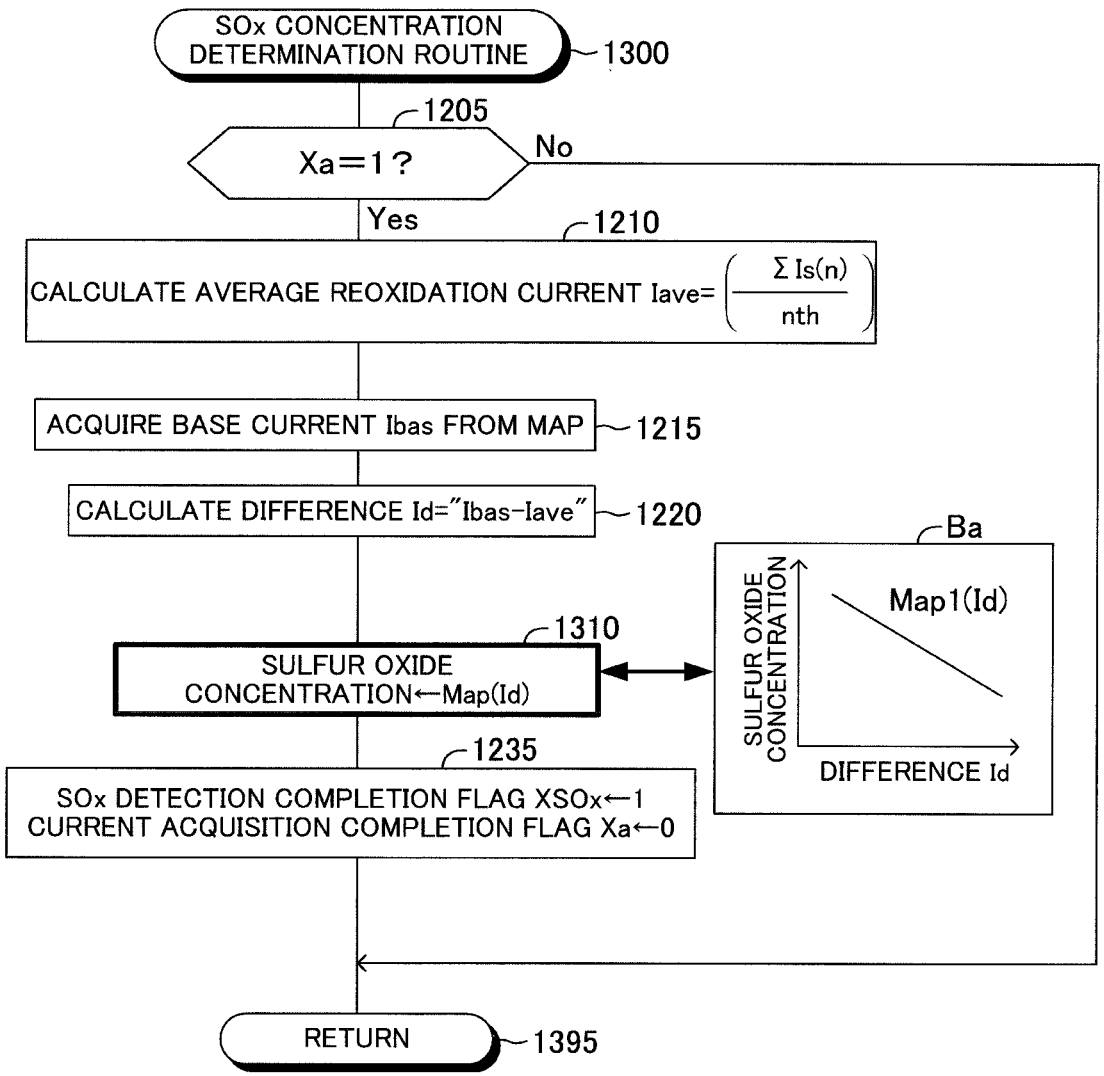
FIG. 13 is a flowchart for illustrating a SOx concentration determination routine executed by the CPU of the ECU illustrated in FIG. 1.

For example, the CPU may be configured so as to execute a SOx concentration determination routine illustrated in FIG. 13 in place of the SOx concentration determination routine illustrated in FIG. 12. The routine illustrated in FIG. 13 is a routine in which "a process of step 1310" is executed in place of the processes of "step 1225, step 1230, and step 1240" illustrated in FIG. 12. Thus, the process of "step 1310" shown in FIG. 13 will be mainly described.

The CPU calculates the difference Id at step 1220 of FIG. 13, and proceeds to step 1310 to apply the difference Id to a lookup table Map1(Id), to thereby acquire the SOx concentration in the exhaust gas. The ROM (storage part) of the ECU 20 stores the "relationship between the difference Id and the SOx concentration of the exhaust gas" as a lookup table Map1(Id) (see a block Ba of FIG. 13). This lookup table can be acquired by performing experiments or the like in advance.

The first modified detection device can provide the same effect as that of the first detection device. Further, the first modified detection device is configured to use the difference Id as the parameter representing the degree of the reoxidation current change that is less likely to be influenced by the oxygen-containing components other than SOx, and acquire the concentration of SOx contained in the exhaust gas using the difference Id and the lookup table Map1(Id) stored in the ROM. Thus, the concentration of the sulfur oxide in the exhaust gas can accurately be detected.

Second Embodiment

A description is now given of a gas detection device (hereinafter sometimes referred to as a "second detection device") according to a second embodiment of the present disclosure. The second detection device is different from the first detection device only in the following point.

The first detection device is configured to perform the first element temperature control while the first detection device performs the voltage increase sweep during executing the applied voltage control for SOx detection. The first detection device is also configured to stop the first element temperature control to perform the second element temperature control while the first detection device performs the voltage decrease sweep during executing the applied voltage control for SOx detection.

In contrast, the second detection device is configured to perform the second element temperature control while the second detection device executes the applied voltage control for SOx detection (that is, while it performs not only the voltage decrease sweep but also the voltage increase sweep).

Hereinafter, this difference will be mainly described.

<Outline of Operation>

Figure 14:
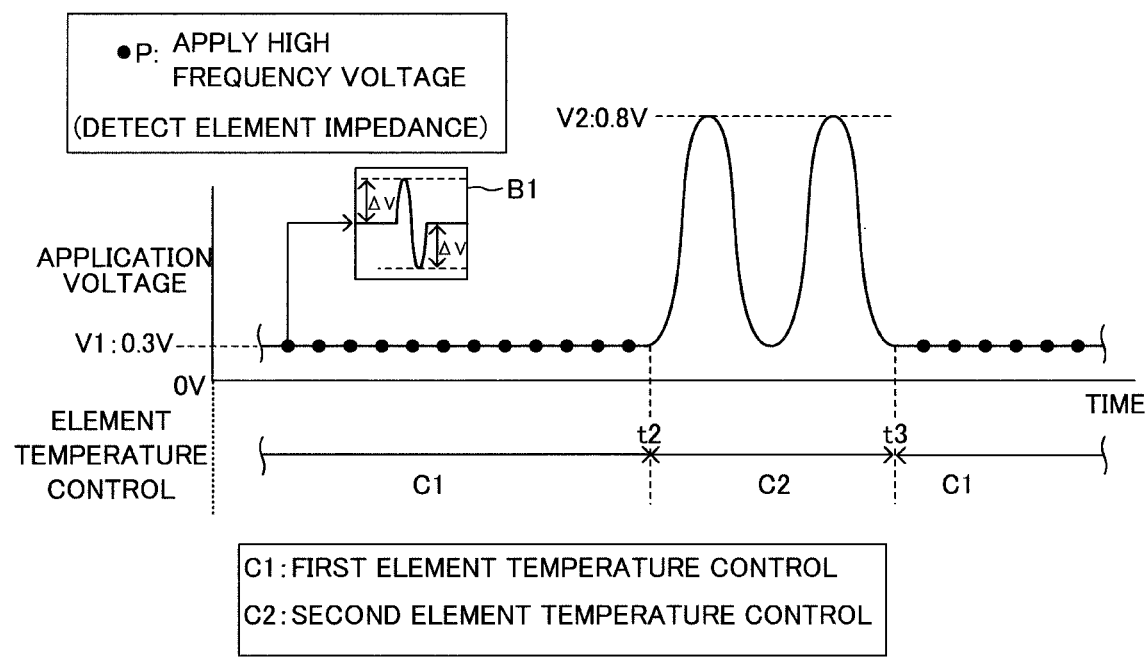
FIG. 14 is a time chart for explaining an overview of the element temperature control operation performed by a CPU of an ECU of the gas detection device according to the second embodiment of the present disclosure.

As illustrated in FIG. 14, while the applied voltage control for SOx detection is performed (the period from time t2 to time t3), the second detection device performs the second element temperature control.

As described above, according to the second element temperature control, the "element impedance detection process" is stopped, and the element impedance is kept at a value detected immediately before the element impedance detection process is stopped. Further, according to the second element temperature control, the energization to the heater 71 is controlled in such a manner that the electric power supplied to the heater 71 is set to a predetermined electric power, thereby controlling the element temperature. Specifically, the second detection device maintains the energization control amount (duty ratio) to the heater 71 to a value which has been set in advance (based on the element impedance detected immediately before the element impedance detection process is stopped) so as to maintain the electric power supplied to the heater 71 at the predetermined electric power. It should be noted that the second detection device may control the electric power supplied to the heater 71 in such a manner that an amount of predetermined electric power is supplied to the heater 71 while "the element impedance detection process" is stopped.

The energization control amount to the heater 71 (or the amount of the predetermined electric power) set in advance is set to an appropriate value so that the element temperature is maintained at the temperature suitable for detecting the SOx concentration detection during the applied voltage control for SOx detection. Similarly to the first detection device, the second detection device may maintain the energization control amount (duty ratio) to the heater 71 to an amount which was set a predetermined time before the element impedance detection process is stopped so as to keep the electric power supplied to the heater 71 at the predetermined electric power.

<Specific Operation>

A description is now given of a specific operation of the second detection device. The CPU of the ECU 20 is configured to execute, every time a predetermined period elapses, routines illustrated by flowcharts of FIG. 10, FIG. 15 instead of FIG. 11, and FIG. 12, using the gas sensor 30. Operations based on the routines illustrated in FIG. 10 and FIG. 12 are the same as the operations based on those routines of the first detection device, and have already been described. Therefore, a description thereof is omitted.

Figure 15:
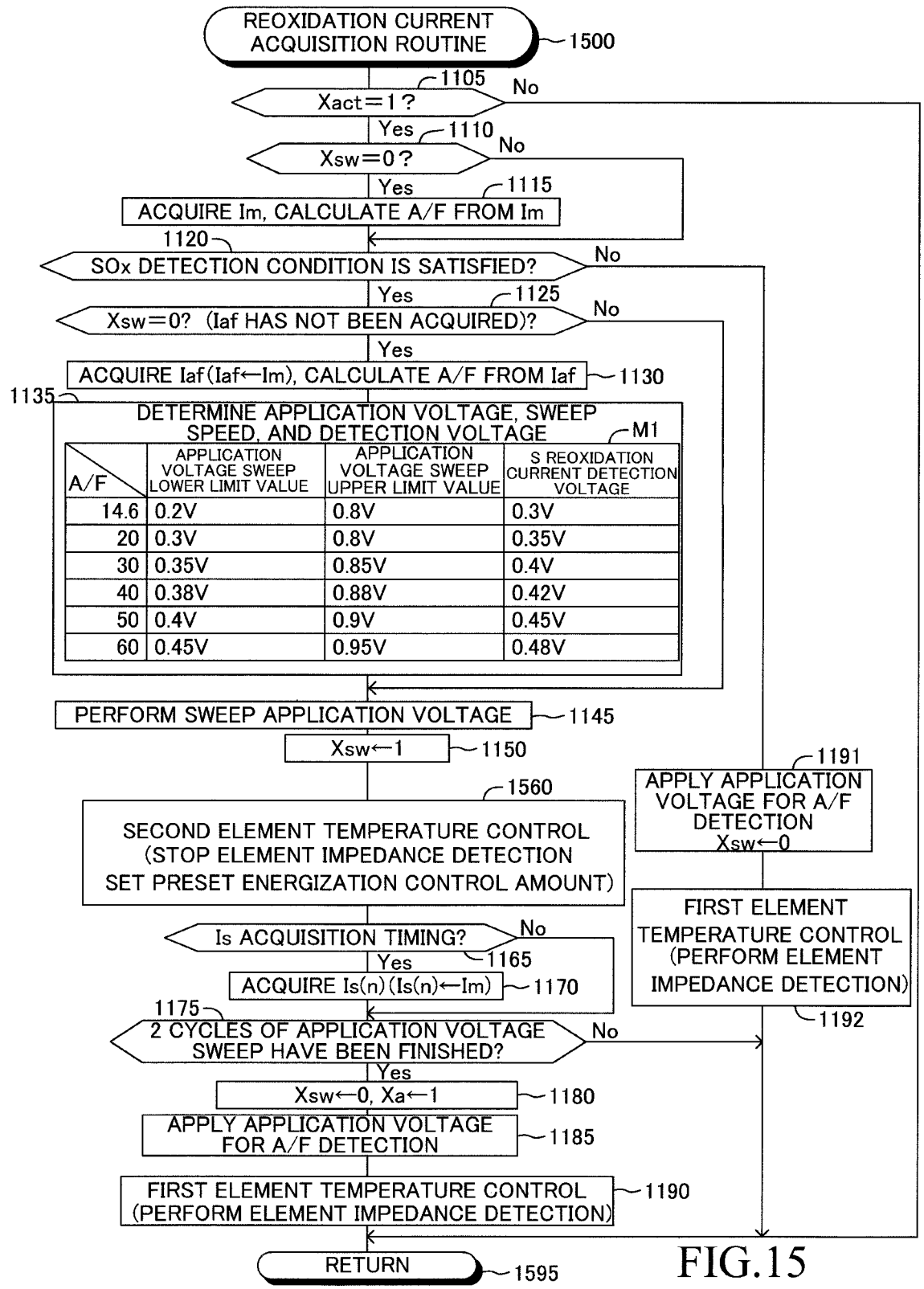
FIG. 15 is a flowchart for illustrating a reoxidation current acquisition routine executed by the CPU of the ECU provided for the gas detection device according to a second embodiment of the present disclosure.

With reference to FIG. 15, a description is now given of the operation of the second detection device. The routine shown in FIG. 15 is different from the routine shown in FIG. 11 only in that the step 1155 of FIG. 11 is deleted, and the step 1160 of FIG. 11 is replaced by the following step 1560.

Step 1560: the CPU performs the second element temperature control.

In other words, the CPU stops the "element impedance detection process", maintains the element impedance at a value detected immediately before the element impedance detection process is stopped, and sets the energization control amount (duty ratio) to the heater 71 to a predetermined energization control amount (duty ratio).

When the CPU has already been performing the second element temperature control at the time point at which the CPU executes the process of step 1560, the CPU continues its second element temperature control. When the CPU has already been performing the first element temperature control at the time point at which the CPU executes the process of step 1560, the CPU stops the first element temperature control to perform the second element temperature control.

According to the routine of FIG. 15, the CPU performs the second element temperature control (refer to step 1560 in FIG. 15) while performing the applied voltage sweep (refer to steps 1145 and 1150 in FIG. 15). The CPU finishes the applied voltage sweeps of two cycles (refer to a "Yes" determination at step 1175 in FIG. 15), stops the second element temperature control to perform the first element temperature control (step 1190 in FIG. 15).

As described above, the second detection device can provide the same effect as that of the first detection device. Further, the second detection device does not perform the "element impedance detection process" not only when the voltage decrease sweep is performed but also when the voltage increase sweep is performed. Therefore, the second detection apparatus can further reduce the "influence on the SOx reaction" due to applying high frequency voltage. As a result of those, the second detection device can accurately detect the SOx concentration.

<Second Modification Example>

A description is now given of a gas detection device (hereinafter sometimes referred to as a "second modified detection device") according to a second modification example of the present disclosure.

The second detection device is configured to compare the magnitude of the difference Id with the threshold difference Idth to thereby determine whether or not SOx having a concentration equal to or higher than the predetermined concentration is contained in the exhaust gas. In contrast, the second modified detection device is configured to acquire the SOx concentration of the exhaust gas based on the difference Id as described below.

For example, the CPU may be configured so as to execute the SOx concentration determination routine illustrated in FIG. 13 in place of the SOx concentration determination routine illustrated in FIG. 12. This routine illustrated in FIG. 13 has already been described. Therefore, a description thereof is omitted.

As described above, the second modified detection device can provide the same effect as that of the second detection device. Further, the second modified detection device is configured to use the difference Id as the parameter representing the degree of the reoxidation current change that is less likely to be influenced by the oxygen-containing components other than SOx, and acquire the concentration of SOx contained in the exhaust gas using the difference Id and the lookup table Map1(Id) stored in the ROM. Thus, the concentration of the sulfur oxide in the exhaust gas can accurately be detected.

<Other Modification Examples>

A description has been given of the respective embodiments of the present disclosure, but the present disclosure is not limited to the respective embodiments, and various modification examples based on the technical idea of the present disclosure may be employed.

When each of the embodiments and the modification examples performs the second element temperature control, it may be configured to maintain the energization control amount (the duty ratio) to the heater 71 at a value determined based on the energization control amount in a predetermined period within the period in which the first element temperature control is being performed (for example, the predetermined period being a period from a "time point a predetermined time before the first element temperature control is stopped" to a "time point Immediately before the first element temperature control is stopped", and the value being an average of the energization control amount (the duty ratio) in the predetermined period), to control the electric power supplied to the heater 71.

The reoxidation current Is is not limited to the "output current Im obtained when the applied voltage Vm becomes equal to the reoxidation current detection voltage Vsen which is the voltage lower than the decomposition start voltage of SOx". That is, each of the respective embodiments and the modification examples described above may acquire, as the reoxidation current Is, a value (current) which correlates with the output current Im in the period in which the voltage decrease sweep is performed, and the applied voltage Vm is lower than the decomposition start voltage of SOx. For example, each of the embodiments may acquire, as the reoxidation current Is, the minimum value of the output current Im in the period in which the applied voltage Vm is within a detection voltage range during the voltage decrease sweep. The detection voltage range is a range from a value equal to or higher than a predetermined voltage which is higher than the lower limit voltage (first voltage V1) of the voltage decrease sweep to a value equal to or lower than a predetermined voltage which is equal to or lower than the decomposition start voltage (0.6 V) of SOx.

The "parameter for detecting the reoxidation current change" is not limited to the difference Id described above, and each of the respective embodiments described above may acquire a value which correlates with the output current Im in the period in which the voltage decrease sweep Is being performed, and the applied voltage Vm is within the detection voltage range.

Further, for example, the voltage waveform of the applied voltage sweep is not limited to the waveforms shown in FIG. 3B or FIG. 3C, but may be an arbitrary waveform (e.g., triangular wave) as long as the voltage forming the waveform continuously changes, and causes the voltage decrease sweep to show the voltage decrease speed which makes the reoxidation current change caused by the reoxidation of the sulfur adsorbed to the first electrode 41a extremely significant from a certain time point during the voltage decrease sweep of the applied voltage sweep.

What is claimed is:

1. A gas detection device, comprising:

an element part, provided in an exhaust gas passage of an internal combustion engine, having an electrochemical cell including: a solid electrolyte body having oxide ion conductivity; a first electrode and a second electrode formed on respective surfaces of said solid electrolyte body; and a diffusion resistance body made of a porous material through which exhaust gas flowing through said exhaust gas passage is allowed to pass, said element part being configured so that said exhaust gas flowing through said exhaust gas passage reaches said first electrode through said diffusion resistance body;

a power supply circuit configured to apply a voltage between said first electrode and said second electrode;

an ammeter configured to detect an output current which is a current flowing between said first electrode and said second electrode;

a heater configured to generate heat having a heat amount corresponding to an electric power supplied thereto to thereby heat said element part; and an electronic control unit including a memory including instructions, the instructions, when executed by a processor of the electronic control unit, causing the electronic control unit to:

control an applied voltage with the power supply circuit, which is said voltage applied between said first electrode and said second electrode, acquire said output current by using the ammeter, and perform, based on said acquired output current, a determination as to whether or not sulfur oxide having a concentration equal to or higher than a predetermined concentration is contained in said exhaust gas or a detection of a concentration of said sulfur oxide in said exhaust gas;

apply a high frequency voltage between said first electrode and said second electrode to thereby detect an impedance of said element part;

perform or stop said detection of said impedance of said element part by applying said high frequency voltage;

control said electric power supplied to said heater to thereby control a temperature of said element part;

perform, with the power supply circuit, applied voltage control for air-fuel ratio detection by setting said applied voltage to a voltage that brings said output current to a limiting current of oxygen, to thereby detect an air-fuel ratio of mixture supplied to said internal combustion engine based on said output current acquired during a period in which said applied voltage control for said air-fuel ratio detection is being performed;

perform, with the power supply circuit, applied voltage control for SOx detection which includes an applied voltage sweep at least for one cycle, said applied voltage sweep including a voltage increase sweep and a voltage decrease sweep, wherein said voltage increase sweep increases said applied voltage from a first voltage to a second voltage, said first voltage is within a first voltage range higher than a lower limit voltage in a region of said limiting current and lower than a decomposition start voltage of said sulfur oxide, and said second voltage is within a second voltage range higher than said decomposition start voltage of said sulfur oxide, and said voltage decrease sweep decreases said applied voltage from said second voltage to said first voltage, acquire, based on said output current, a parameter correlating with a degree of a change in said output current caused by a current flowing between said first electrode and said second electrode owing to a phenomenon that sulfur adsorbed to said first electrode returns to sulfur oxide through a reoxidation reaction on said first electrode when said applied voltage becomes lower than said decomposition start voltage of said sulfur oxide while said voltage decrease sweep is being performed, said change in said output current being larger as said concentration of said sulfur oxide contained in said exhaust gas being larger;

perform, based on said acquired parameter, said determination or said detection;

perform, while said applied voltage control for said air-fuel ratio detection is being performed, a first element temperature control to control said temperature of said element part by detecting said impedance of said element part through applying said high frequency voltage and by controlling said electric power supplied to said heater based on a comparison of said detected impedance of said element part and a target impedance; and stop applying said high frequency voltage to stop detecting said element impedance, and perform a second element temperature control to set said electric power supplied to said heater to a predetermined electric power, while said applied voltage control for said SOx detection is being performed and at least said voltage decrease sweep is being performed.

2. The gas detection device according to claim 1, wherein the instructions, when executed by the processor of the electronic control unit, cause the electronic control unit to:

perform said first element temperature control when said voltage increase sweep is being performed while said applied voltage control for SOx detection is being performed.

3. The gas detection device according to claim 1, wherein the instructions, when executed by the processor of the electronic control unit, cause the electronic control unit to:

change an energization control amount to thereby control said electric power supplied to said heater; and perform said second element temperature control:

by keeping said energization control amount at an amount at a time point a predetermined time before said first element temperature control is stopped; or by keeping said energization control amount at a preset constant amount.

4. The gas detection device according to claim 1, wherein instructions, when executed by the processor of the electronic control unit, cause the electronic control unit to:

perform said second element temperature control so as to supply electric power having an amount which is set in advance to said heater in a period when said element impedance detection is stopped.

5. The gas detection device according to claim 1, wherein, a voltage decrease speed of said voltage decrease sweep is set at a speed which has a rate of said reoxidation reaction quickly increase when and immediately after said applied voltage becomes a voltage in said first voltage range and higher than said first voltage.

* * * * *

UNITED STATES PATENT AND TRADEMARK OFFICE
CERTIFICATE OF CORRECTION

PATENT NO. : 10,677,750 B2
APPLICATION NO. : 15/892851
DATED : June 9, 2020
INVENTOR(S) : Keiichiro Aoki It is certified that error appears in the above-identified patent and that said Letters Patent is hereby corrected as shown below:

On the Title Page

Item (72), inventor information, inventor city, delete "Shizuoka-ken" and insert --Sunto-gun Shizuoka-ken--, therefor.

In the Specification

In Column 1, Line(s) 50, delete "actin" and insert --action--, therefor.

In Column 2, Line(s) 57, delete "elated-art" and insert --related-art--, therefor.

In Column 3, Line(s) 2, delete ""present" and insert --present--, therefor.

In Column 8, Line(s) 6, delete "Illustrating" and insert --illustrating--, therefor.

In Column 10, Line(s) 9, delete "Sib" and insert --51b--, therefor.

In Column 12, Line(s) 53, delete "t11" and insert --t1--, therefor.

In Column 15, Line(s) 5, after "compounds", delete "Is" and insert --is--, therefor.

In Column 20, Line(s) 55, delete "block 81" and insert --block B1--, therefor.

In Column 20, Line(s) 65 & 66, delete "Information" and insert --information--, therefor.

In Column 22, Line(s) 35, delete "stopped"" and insert --stopped--, therefor.

In Column 25, Line(s) 6, delete "Internal" and insert --internal--, therefor.

Signed and Sealed this
Eleventh Day of August, 2020

Andrei Iancu
*Director of the United States Patent and Trademark Office*

In Column 32, Line(s) 30, delete "Immediately" and insert --immediately--, therefor.

In Column 32, Line(s) 59, after "sweep", delete "Is" and insert --is--, therefor.